US005914317A

United States Patent [19]

Burgeson et al.

[11] Patent Number: 5,914,317

[45] Date of Patent: Jun. 22, 1999

[54] B1K CHAIN OF LAMININ AND METHODS OF USE

[75] Inventors: Robert E. Burgeson, Marblehead; David Wolfe Wagman, Melrose, both of Mass.

[73] Assignees: The General Hospital Corporation, Boston, Mass.; The State of Oregon Acting By & Thru The State Board . . ., Portland, Oreg.

[21] Appl. No.: 08/735,893

[22] Filed: Oct. 23, 1996

Related U.S. Application Data

[62] Division of application No. 08/144,121, Oct. 27, 1993, Pat. No. 5,610,031.

[51] Int. Cl.[6] .......................... C07K 14/00; C07K 14/78; A61K 38/39

[52] U.S. Cl. .................................... 514/12; 512/2; 512/8; 530/300; 530/324; 530/350; 530/353; 530/395

[58] Field of Search .................................... 530/300, 324, 530/350, 353, 395; 514/2, 8, 12

[56] References Cited

U.S. PATENT DOCUMENTS 5,003,044 3/1991 Hunter et al. .......................... 530/326

FOREIGN PATENT DOCUMENTS

92/17498 10/1992 WIPO .
WO 92/17498 10/1992 WIPO .

OTHER PUBLICATIONS

D. Gerecke et al. "cDNAs Encoding for Two of the Chains of the Anchoring Filament Protein Kalinin Show Similarity to the Laminin B1 and B2 Chains", Matrix 13(1): 20–21, Jan. 1993.

D. Gerecke et al. "The Anchoring Filament Protein Kalinin is a Laminin Isotype", Exp. Eye Res. 55 (Suppl. 1): S73, Sep. 1992.

J.C. Schittny et al. "Terminal Short–Arm Domains of Basement Membrane Laminin Are Critical For Its Self–Assembly", J. Cell Biol. 110(3) 825–832, Mar. 1990.

U.S. application No. 08/141,233, Burgeson et al., filed Oct. 1993.

Aratani et al., "Enhanced Synthesis and Secretion of Type IV Collagen and Entactin during Adipose Conversion of 3T3–L1 Cells and Production of Unorthodox Laminin Complex" *The Journal of Biological Chemistry*, vol. 263, No. 31, pp. 16163–16169, (1988).

Beck et al., "Structure and Function of Laminin: Anatomy of a Multidomain Glycoprotein" *The FASEB Journal*, vol. 4, pp. 148–160, (1990).

Berger et al. (eds) "Guide to Molecular Cloning Techniques", *Meth. in Enzymology* 152:316–703 ((1987).

Cooper et al., "Studies on the Biosynthesis of Laminin by Murine Parietal Endoderm Cells" *European Journal of Biochemistry*, vol. 119, pp. 189–197, (1981).

Davis et al., "Isolation and Characterization of Rat Schwannoma Neurite–promoting Factor: Evidence that the Factor Contains Laminin" *The Journal of Neuroscience*, vol. 5, No. 10, pp. 2662–2671, (1985).

Edgar et al., "Structural Requirements for the Stimulation of Neurite Outgrowth by Two Variants of Laminin and Their Inhibition by Antibodies" *The Journal of Cell Biology*, vol. 106, pp. 1299–1306, (1988).

Ehrig et al., "Merosin, A Tissue–Specific Basement Membrane Protein, is a Laminin–Like Protein" *Proceedings of the National Academy of Sciences*, vol. 87, pp. 3264–3268, (1990).

Engvall et al., "Distribution and Isolation of Four Laminin Variants; Tissue Restricted Distribution of Heterotrimers Assembled From Five Different Subunits" *Cell Regulation*, vol. 1, pp. 731–740, (1990).

Engvall et al., "Mapping of Domains in Human Laminin Using Monoclonal Antibodies: Localization of the Neurite–promoting Site" *The Journal of Cell Biology*, vol. 103, No. 6, pp. 2457–2465, (1986).

Frenette et al., "Biosynthesis and Secretion of Laminin and Laminin–associated Glycoproteins by Nonmalignant and Malignant Human Keratinocytes: Comparison of Cell Lines from Primary and Secondary Tumors in the Same Patient" *Cancer Res*, vol. 48, pp. 5193–5202, (1988).

Gerecke et al., "cDNA's Encoding for the Three Chains of the Anchoring Filament Protein Kalinin Show Similarity to the Laminin A B1 and B2 Chains", *Mol. Biol. Cell*, vol. 3, (suppl.), p. # 1A, (1992).

Hunter et al., "Laminin Chain Assembly by Triple and Double Stranded Coiled–Coil Structures", *The Journal of Biological Chemistry*, vol. 267, No. 9, pp. 6006–6011, (1992).

Hunter et al., "Expression of S–Laminin and Laminin in the Developing Rat Central Nervous System" *The Journal of Comparative Neurology*, vol. 323, pp. 238–251, (1992).

Hunter et al., "An LRE (Leucine–Arginine–Glutamate)–dependent Mechanism for Adhesion of Neurons to S–laminin" *The Journal of Neuroscience*, vol. 11, No. 12, pp. 3960–3671, (1991).

Hunter et al., "Primary Sequence of a Motor Neuron–Selective Adhesive Site in the Synaptic Basal Lamina Protein S–Laminin" *Cell*, vol. 59, pp. 905–913, (1989).

Liesi et al., "Glial Cells of Mammalian Brain Produce a Variant Form of Laminin" *Experimental Neurology*, vol. 105, pp. 86–92, 1989.

Marinkovich et al., "The Anchoring Filament Protein Kalinin Is Synthesized and Secreted as a High Molecular Weight Precursor", *The Journal of Biological Chemistry*, vol. 267, No. 25, pp. 17900–17906, (1992).

Marinkovich et al., "The Dermal–Epidermal Junction of Human Skin Contains a Novel Laminin Variant" *The Journal of Cell Biology*, vol. 119, No. 3, pp. 695–703, 1992.

Marinkovich et al., "Characterization of a Novel Laminin Isoform Produced by Human Keratinocytes In Vitro", *Clinical Research*, vol. 39, No. 2, p. # 565A, (1991).

(List continued on next page.)

*Primary Examiner*—Rebecca E. Prouty
*Attorney, Agent, or Firm*—Fish & Richardson PC

[57] ABSTRACT

Recombinant laminin B1k and fragments thereof.

9 Claims, 13 Drawing Sheets

OTHER PUBLICATIONS

Morita et al., "Post–translational Assembly and Glycosylation of Laminin Subunits in Parietal Endoderm–like F9 Cells" *Biochemistry Journal*, vol. 229, pp. 259–264, (1985).

Paulsson et al., "Mouse Heart Laminin" *The Journal of Biological Chemistry*, vol. 264, No. 31, pp. 18726–18732, 1989.

Peters et al., "The Biosynthesis, Processing, and Secretion of Laminin by Human Choriocarcinoma Cells" *The Journal of Biological Chemistry*, vol. 260, No. 27, pp. 14732–14742, (1985).

Rouselle et al., "Kalinin: An Epithelium–Specific Basement Membrane Adhesion Molecule That Is a Component of Anchoring Filaments" *Journal Cell Biology*, vol. 114, pp. 567–576, (1991).

Sanes et al., "S–Laminin" *Cold Spring Harbor Symposia on Quantitative Biology*, vol. 55, pp. 419–430, (1990).

Wewer et al., "Human Laminin Isolated in a Nearly Intact, Biologically Active Form from Placenta by Limited Proteolysis" *The Journal of Biological Chemistry*, vol. 258, No. 20, pp. 12654–12660, (1983).

Woodley et al., "Laminin Inhibits Human Keratinocyte Migration" *Journal of Cellular Physiology*, vol. 136, pp. 140–146, (1988).

DOMAIN VI

```
Blk    1      QQACSRGACYPPVGDLLVGRTRFLRASSTCGLTKPETYC  TQYGEWQMKCCKCDSRQPH    NYYSHRVE
                :|  | |||: ||||:||   |   ||||| ||| ||   :  | : ||  |:| :|     |  || :|
Ble    1 QEPEFSYGCAEGSCYPATGDLLIGRAQKLSVTSTCGLHKPEPYCIVSHLQE DKKCFICNSQDPYHETLNPDSHLIE

Blk   67 NVASSSGPMR   WWQSQNDVNPVSLQLDLDRRFQLQEVMMEFPGAHAAGMLIERSSDFGKTWRVYQYLAADCTSTF
         ||    :| |   ||||:|:|: | :||||:  |::  ::| |   ::|:||||||||||||| || |:| ||   |
Ble   77 NVVTTFAPNRLKIWWQSENGVENVTIQLDLEAEFHFTHLIMTFKTFRPAAMLIERSSDFGKTWGVYRYFAYDCEASF

Blk  141 PRVRQGRPQSWQDVRCQSLPQRPNARLNGGKVQLNLMDLVSGIPATQSQKIQEVGEITNLRVNFTRLAPV      P
         | :  |     :|: |:|          :| | :  :|     |    | :||::  |||||: | :| :
Ble  154 PGISTGPMKKVDDIICDS RYSDIEPSTEGEVIFRALDPAFKIEDPYSPRIQNLLKITNLRIKFVKLHTLGDNLLDS

Blk  212 KLDHPPSAYYAVSQLRLQGS
         :::     |||| :: : |
Ble  230 RMEIREKYYYAVYDMVVRGN
```

FIG. 3A

DOMAIN III/V

```
              CFCHGHADRCAPKPGASAGSTAVQVHDVCVCQHNTAGPNCERCAPFYNNRPWRPAE
              ||| |||  |||  |     :   :: ||: |:| ||| | ||| |  ||:: ||||||
              CFCYGHASECAPVDGFNEEVEGM VHGHCMCRHNTKGLNCELCMDFYHDLPWRPAE
B1k  288 GQDAHECQRCDCNGHSENCHFDPAVFAASQGAYGGVCDNCRDHTEGKNCERCQLHYFRNRRPGASIQETCISCECDP
          | : : | :|:||:||  |||| ||: |        |||||:|  :| |:||| |   |: :   :    :|  | |||
B1e  305 GRNSNACKKCNCNEHSISCHFDMAVYLATGNVSGGVCDDCQHNTMGRNCEQCKPFYYQHPERDIRDPNFCERCTCDP

B1k  365 DGQWAGAPCDP            VTGQCVCKEHVQGERCDLCKPGFTGLTYANPQGCHR
          |   :: ||            : ||| || :|:||:||:|| || :|    :| ||
B1e  382 AGSQNEGICDSYTDFSTGLIAGQCRCKLNVEGEHCDVCKEGFYDLSSEDPFGCKS
```

FIG. 3B

DOMAIN II

```
                                                                          CDCNILPSRRL
                                                                          | || |
                                                            -569 res-  CVCNYLGTVQE
Blk   423        PCDEESGRCLCLPNVGGPKCDQCAPYHWKLASGQGCEPCACDPHNSLSPQCNQFTGQCPCREGFGGLMCS
                  ||   | |||||||| |  || ||| | |||| ||:|| |:: :|::| ||:||||| |  |||| ||
Ble  1017 HCNGSDCQCDKATGQCLCLPNVIGQNCDRCAPNTWQLASGTGCDPCNCNAAHSFGPSCNEFTGQCQCMPGFGGRTCS

Blk   493 AAAIRQCPDRTYGDVATGCRACDCDFRGTEGPGCDKASG VLCRPGLTGPRCDQCQRGYCNRYPVCVA CHPCFQTY
                :| :  :||   :||||||| || | | ||     |  :|  |: ||||| | |||:  :| | : || || :
Ble  1094      ECQELFWGDPDVECRACDCDPRGIETPQCDQSTGQCVCVEGVEGPRCDKCTRGYSGVFPDCTP CHQCFALW

Blk   568 DADLREQALRFGRLPNATASLWSGPGLEDRGLASRILDAKSKIEQIRAVL  SSPAVTEQEVAQVASAILSLRRTLQ
          | : |  | |: :  | :  ::      :    |: :|: :| | :|::: :          | : :
Ble  1165 DVIIAELTNRTHRFLEKAKALKISGVIG  PYRETVDSVERKVSEIKDILAQSPAAEPLKNIGNLFEEAEKLIKDVT

Blk   643 GL  QLDLPLEEET   LSLPRDLESLDRSFNGLLTMYQRKREQFEKISSADPSGAFRMLSTAYEQSAQAAQQVS
          ::  |::: | : |   | :::|:||:   ::|        ||:| |   | ||:  :    :: | :| : |
Ble  1240 EMMAQVEVKLSDTTSQSNSTAKELDSLQTEAESLDNTVKELAEQLEFIKNSDIRGALDSITKYFQMSLEAEERVNAS

Blk   713            DSSRLLDQLRDSRREAERLVRQAGGGGGTGSPKLVA  LRLEMSSLPDLTPTFNKL
                     :|  : | : |   | |   ::  :: :     | :   |::|  :::|
Ble  1317 TTEPNSTVEQSALMRDRVEDVMMERESQFKEKQEEQARLLDELAGKLQSLDLSAAAEMT
```

FIG. 3C

DOMAIN I

ALPHA DOMAIN

```
Blk   778  ISCPGELCPQDNG   TACASRC RGVTLPRAGGAFLMAGQVAEQLRASMPAPA  TRQMIRAAEESASQIQSSAQRLET
                 ::  :  |||    :  ||  |  |  ||  :  ::  :::          ||       |:    |||   :
Ble  1387  TECGGPNCRTDEGERKCGGPGC GGLVTVAHNAWQKAMDLDQDVLSALAEVEQLSKMVSEAKLRADEAKQSAEDILL

Blk   851  QVSASRSQMEEDVRRTRLLIQQVRDFLTDPDTDAATIQEVRRAVLALWLPTDSATVLQKMNEIQAIAARLPNVDLVL
            ||   :  |||    :|::||::  |  :  | :    ||   :    :|         ::  :::|
Ble  1463  KTNATKEKMDKSNEELRNLIKQIRNFLTQDSADLDSIEAVANEVLKMEMPSTPQQLQNLTEDIRERVESLSQVEVIL

Blk   928  SQTKQDIGGARRLQAEAEEAARSRAHAVEGQVEDVVGNLRQ         GTVALQEAQDTMQGTSRSLRLLIQDRVAEVQ
             ::   ||     |  | |    |    :  |:  |                 ||  :  |::: :|||       ||
Ble  1540  QHSAADIARAEMLLEEAKRASKSATDVKVTADMVKEALEEAEKAQVAAEEKAIKQADEDIQGTQNLLTSIESETAASE

Blk   998  QVLGQQKLVTSMTKQLGDFWTRMEELRHQARQQGAEAVQAQQLAEGASEQALSAQEGFE  RIKQKYAELKDRLGQSS
                    ::    :|||::  |  |||  :  |     |   :                       :: : |||  ::
Ble  1617  ETL        FNASQRISELERNVEELKRKAAQNSGEAEYIERKVVYTVKQSAEDVKKTLDGELDEKYKKVENLIAKKT
                                                                                        (SEQ.I.D.NO.3)

Blk  1074  MLGEQGAR  IQSVKTEAEELFGETMEMMDRMKDMELELLRAAGH HAALSDLTGLEKRVEQIRDHINGRVLYYSTCK
             :  |    |     ||  |:::   ::   |||                :|   ||   :    ||         |||
Ble  1688  EESADARRKAEMLQNEAKTLLAQANSKLQLLRDLERKYEDNQRYLEDKAQELARLEGEVRSLLKDISQKVAVYSTCL
                                                                                        (SEQ.I.D.NO.4)
```

|  |
|---|
| CGNSRQMACTP |
| || |
| CGTPPGASCSE |

FIG. 3D

DOMAINS (IN AMINO ACID RESIDUES)

| | VI | V | IV | III | II | α | I | TOTAL |
|---|---|---|---|---|---|---|---|---|
| LAMINEN B1e | 249 | 278 | 227 | 404 | 218 | 33 | 356 | 1765 |
| LAMINEN B1k | 231 | 180 | 0 | 148 | 207 | 31 | 351 | 1148 |

| | | | | | | | | |
|---|---|---|---|---|---|---|---|---|
| PERCENT AMINO ACID RESIDUE IDENITY | 41.1 | 46.1 | - | 51.4 | 20.3 | 29.0 | 21.7 | 34.1 |

```
Blk    1          QQA*SR*A***PV****V**TRF*RAS***** T***T****TQYG*WQM**CK***RQ
Ble^   1      QEPEFSYGCAEGSCYPATGDLLIGRAQKLSVTSTCGLHKPEPYCIVSHLQE DKKCFICNSQD
Bls>   1     QVPSLDVP**SR***********V****DR*TAS******S*Q*********D E****L*D*RR

Blk   57     *H     *YY**RV***ASSSG*M*    ****Q*D*NP*SL****DRR*OLOEVM*E*PGAHA*G
Ble   64     PYHETLNPDSHLIENVVTTFAPNRLKIWWQSENGVENVTIQLDLEAEFHFTHLIMTFKTFRPAA
Bls   65     *FSARD**N**RIQ****S***Q*RTA********PM*************************

Blk  114     ************R**Q*L*A**TST**RVRQ*RPQSWQ*VR*Q*LPORPNARLNG*K*OLNLM
Ble  128     MLIERSSDFGKTWGVYRYFAYDCEASFPGISTGPMKKVDDIICDS RYSDIEPSTEGEVIFRAL
Bls  129     **V***A***R**R*****S***G*D****PLA*PRRW**VV*E*****E**********Y*V*

Blk  178     *LVSG**ATO*OK**EVGE**********APV        PKLDHPPSA****SOLRLO*S*SEQ.I.D.NO.5)
Ble  191     DPAFKIEDPYSPRIQNLLKITNLRIKFVKLHTLGDNLLDSRMEIREKYYYAVYDMVVRGN(SEQ.I.D.NO.6)
Bls  192     ***IP*P****S***********VNLTR**********P*R*********L*EL*I*** (SEQ.I.D.NO.7)
```

^PIKKARAINEN et al, 1987
>HUNTER et al, 1989

FIG. 5

| | | | |
|---|---|---|---|
| RAT | LAMBIS* | RES.#1637 | EALKLKRAGNSLAASTAEETAGSAQSRAREAEKQLREQVG (SEQ. I.D. NO. 8) |
| HUMAN | LAMBIS | PEPTIDE | AGNSLAASTAEETAGSAQGRAQEA (SEQ. I.D. NO. 9) |
| HUMAN | LAMBIK | RES.#1021 | EELRHQARQQGAEAVQAQQLAEGASEQALSAQEGFERIKQ (SEQ. I.D. NO. 10) |
| HUMAN | LAMB2T^ | RES.# 428 | TGDCYSGDENPDIECADCPIGFYNDPHDPRSCKPCPCHNG (SEQ. I.D. NO. 11) |
| HUMAN | LAMB2T | PEPTIDE | DENPDIECADCPIGFYN (SEQ. I.D. NO. 12) |
| HUMAN | LAMB2T^ | RES.#1083 | KVDTRAKNAGVTIQDTLNTLDGLLHLMDQPLSVDEEGLVL (SEQ. I.D. NO. 13) |
| HUMAN | LAMB2T | PEPTIDE | NAGVTIQDTLNTLDGLLHLMDQPLS (SEQ. I.D. NO. 14) |

*HUNTER ET AL, 1989
^KALLUNKI ET AL, 1992

FIG. 6

| | PERCENT IDENTITY | PERCENT SIMILARITY |
|---|---|---|
| HUMAN LAMININ B1e | 34.1 | 53.6 |
| HUMAN LAMININ B2e | 28.4 | 49.6 |
| HUMAN LAMININ B2t | 21.4 | 43.1 |
| RAT LAMININ B1s | 37.1 | 56.2 |

FIG. 7

SEQUENCE LISTING

```
(1) GENERAL INFORMATION:

   (iii) NUMBER OF SEQUENCES: 14


(2) INFORMATION FOR SEQ ID NO:1:

     (i) SEQUENCE CHARACTERISTICS:
          (A) LENGTH: 3931 base pairs
          (B) TYPE: nucleic acid
          (C) STRANDEDNESS: single
          (D) TOPOLOGY: linear

    (ii) MOLECULE TYPE: cDNA

    (ix) FEATURE:
          (A) NAME/KEY: CDS
          (B) LOCATION: 122..3617
```

(ix) FEATURE:
(A) NAME/KEY: mat_peptide
(B) LOCATION: 173..3617

(xi) SEQUENCE DESCRIPTION: SEQ ID NO:1:

```
GGGCGTGGAG GAGGACTGTA TCTCTGGATG CCTGGGGCCT GGTTTCAGGG CCTGATTTAT     60

TCCTCTTCCT GGGAGCTCAC TCAGGAAAGG TCCTTTCTGG GGATCACCCC ATTGGCTGAA    120

G ATG AGA CCA TTC TTC CTC TTG TGT TTT GCC CTG CCT GGC CTC CTG        166
  Met Arg Pro Phe Phe Leu Leu Cys Phe Ala Leu Pro Gly Leu Leu
  -17     -15                 -10                  -5

CAT GCC CAA CAA GCC TGC TCC CGT GGG GCC TGC TAT CCA CCT GTT GGG      214
His Ala Gln Gln Ala Cys Ser Arg Gly Ala Cys Tyr Pro Pro Val Gly
        1               5                  10

GAC CTG CTT GTT GGG AGG ACC CGG TTT CTC CGA GCT TCA TCT ACC TGT      262
Asp Leu Leu Val Gly Arg Thr Arg Phe Leu Arg Ala Ser Ser Thr Cys
 15                  20                  25                  30

GGA CTG ACC AAG CCT GAG ACC TAC TGC ACC CAG TAT GGC GAG TGG CAG      310
Gly Leu Thr Lys Pro Glu Thr Tyr Cys Thr Gln Tyr Gly Glu Trp Gln
                35                  40                  45

ATG AAA TGC TGC AAG TGT GAC TCC AGG CAG CCT CAC AAC TAC TAC AGT      358
Met Lys Cys Cys Lys Cys Asp Ser Arg Gln Pro His Asn Tyr Tyr Ser
            50                  55                  60

CAC CGA GTA GAG AAT GTG GCT TCA TCC TCC GGC CCC ATG CGC TGG TGG      406
His Arg Val Glu Asn Val Ala Ser Ser Ser Gly Pro Met Arg Trp Trp
        65                  70                  75

CAG TCC CAG AAT GAT GTG AAC CCT GTC TCT CTG CAG CTG GAC CTG GAC      454
Gln Ser Gln Asn Asp Val Asn Pro Val Ser Leu Gln Leu Asp Leu Asp
    80                  85                  90

AGG AGA TTC CAG CTT CAA GAA GTC ATG ATG GAG TTC CCA GGG GCC CAT      502
Arg Arg Phe Gln Leu Gln Glu Val Met Met Glu Phe Pro Gly Ala His
 95                 100                 105                 110

GCT GCC GGC ATG CTG ATT GAG CGC TCC TCA GAC TTC GGT AAG ACC TGG      550
Ala Ala Gly Met Leu Ile Glu Arg Ser Ser Asp Phe Gly Lys Thr Trp
                115                 120                 125

CGA GTG TAC CAG TAC CTG GCT GCC GAC TGC ACC TCC ACC TTC CCT CGG      598
Arg Val Tyr Gln Tyr Leu Ala Ala Asp Cys Thr Ser Thr Phe Pro Arg
            130                 135                 140

GTC CGC CAG GGT CGG CCT CAG AGC TGG CAG GAT GTT CGG TGC CAG TCC      646
Val Arg Gln Gly Arg Pro Gln Ser Trp Gln Asp Val Arg Cys Gln Ser
        145                 150                 155

CTG CCT CAG AGG CCT AAT GCA CGC CTA AAT GGG GGG AAG GTC CAA CTT      694
Leu Pro Gln Arg Pro Asn Ala Arg Leu Asn Gly Gly Lys Val Gln Leu
    160                 165                 170

AAC CTT ATG GAT TTA GTG TCT GGG ATT CCA GCA ACT CAA AGT CAA AAA      742
Asn Leu Met Asp Leu Val Ser Gly Ile Pro Ala Thr Gln Ser Gln Lys
175                 180                 185                 190

ATT CAA GAG GTG GGG GAG ATC ACA AAC TTG AGA GTC AAT TTC ACC AGG      790
Ile Gln Glu Val Gly Glu Ile Thr Asn Leu Arg Val Asn Phe Thr Arg
                195                 200                 205

CTG GCC CCT GTG CCC AAA CTG GAC CAC CCT CCC AGC GCC TAC TAT GCT      838
Leu Ala Pro Val Pro Lys Leu Asp His Pro Pro Ser Ala Tyr Tyr Ala
            210                 215                 220

GTG TCC CAG CTC CGT CTG CAG GGG AGC TGC TTC TGT CAC GGC CAT GCT      886
Val Ser Gln Leu Arg Leu Gln Gly Ser Cys Phe Cys His Gly His Ala
        225                 230                 235

GAT CGC TGC GCA CCC AAG CCT GGG GCC TCT GCA GGC TCC ACC GCT GTG      934
Asp Arg Cys Ala Pro Lys Pro Gly Ala Ser Ala Gly Ser Thr Ala Val
    240                 245                 250

CAG GTC CAC GAT GTC TGC GTC TGC CAG CAC AAC ACT GCC GGC CCA AAT      982
```

-continued

```
Gln Val His Asp Val Cys Val Cys Gln His Asn Thr Ala Gly Pro Asn
255                 260                 265                 270

TGT GAG CGC TGT GCA CCC TTC TAC AAC AAC CGG CCC TGG AGA CCG GCG      1030
Cys Glu Arg Cys Ala Pro Phe Tyr Asn Asn Arg Pro Trp Arg Pro Ala
                275                 280                 285

GAG GGC CAG GAC GCC CAT GAA TGC CAA AGG TGC GAC TGC AAT GGG CAC      1078
Glu Gly Gln Asp Ala His Glu Cys Gln Arg Cys Asp Cys Asn Gly His
            290                 295                 300

TCA GAG AAC TGT CAC TTT GAC CCC GCT GTG TTT GCC GCC AGC CAG GGG      1126
Ser Glu Asn Cys His Phe Asp Pro Ala Val Phe Ala Ala Ser Gln Gly
        305                 310                 315

GCA TAT GGA GGT GTG TGT GAC AAT TGC CGG GAC CAC ACC GAA GGC AAG      1174
Ala Tyr Gly Gly Val Cys Asp Asn Cys Arg Asp His Thr Glu Gly Lys
    320                 325                 330

AAC TGT GAG CGG TGT CAG CTG CAC TAT TTC CGG AAC CGG CGC CCG GGA      1222
Asn Cys Glu Arg Cys Gln Leu His Tyr Phe Arg Asn Arg Arg Pro Gly
335                 340                 345                 350

GCT TCC ATT CAG GAG ACC TGC ATC TCC TGC GAG TGT GAT CCG GAT GGG      1270
Ala Ser Ile Gln Glu Thr Cys Ile Ser Cys Glu Cys Asp Pro Asp Gly
                355                 360                 365

CAG TGG GCA GGG GCT CCC TGT GAC CCA GTG ACC GGG CAG TGT GTG TGC      1318
Gln Trp Ala Gly Ala Pro Cys Asp Pro Val Thr Gly Gln Cys Val Cys
            370                 375                 380

AAG GAG CAT GTG CAG GGA GAG CGC TGT GAC CTA TGC AAG CCG GGC TTC      1366
Lys Glu His Val Gln Gly Glu Arg Cys Asp Leu Cys Lys Pro Gly Phe
        385                 390                 395

ACT GGA CTC ACC TAC GCC AAC CCG CAG GGC TGC CAC CGC TGT GAC TGC      1414
Thr Gly Leu Thr Tyr Ala Asn Pro Gln Gly Cys His Arg Cys Asp Cys
    400                 405                 410

AAC ATC CTG CCC TCC CGG AGA CTG CCG TGT GAC GAG GAG AGT GGG CGC      1462
Asn Ile Leu Pro Ser Arg Arg Leu Pro Cys Asp Glu Glu Ser Gly Arg
415                 420                 425                 430

TGC CTT TGT CTG CCC AAC GTA GGT GGT CCC AAA TGT GAC CAG TGT GCT      1510
Cys Leu Cys Leu Pro Asn Val Gly Gly Pro Lys Cys Asp Gln Cys Ala
                435                 440                 445

CCC TAC CAC TGG AAG CTG GCC AGT GGC CAG GGC TGT GAA CCG TGT GCC      1558
Pro Tyr His Trp Lys Leu Ala Ser Gly Gln Gly Cys Glu Pro Cys Ala
            450                 455                 460

TGC GAC CCG CAC AAC TCC CTC AGC CCA CAG TGC AAC CAG TTC ACA GGG      1606
Cys Asp Pro His Asn Ser Leu Ser Pro Gln Cys Asn Gln Phe Thr Gly
        465                 470                 475

CAG TGC CCC TGT CGG GAA GGC TTT GGT GGC CTG ATG TGC AGC GCT GCA      1654
Gln Cys Pro Cys Arg Glu Gly Phe Gly Gly Leu Met Cys Ser Ala Ala
    480                 485                 490

GCC ATC CGC CAG TGT CCA GAC CGG ACC TAT GGA GAC GTG GCC ACA GGA      1702
Ala Ile Arg Gln Cys Pro Asp Arg Thr Tyr Gly Asp Val Ala Thr Gly
495                 500                 505                 510

TGC CGA GCC TGT GAC TGT GAT TTC CGG GGA ACA GAG GGC CCG GGC TGC      1750
Cys Arg Ala Cys Asp Cys Asp Phe Arg Gly Thr Glu Gly Pro Gly Cys
                515                 520                 525

GAC AAG GCA TCA GGC GTG CTC TGC CGC CCT GGC TTG ACC GGG CCC CGC      1798
Asp Lys Ala Ser Gly Val Leu Cys Arg Pro Gly Leu Thr Gly Pro Arg
            530                 535                 540

TGT GAC CAG TGC CAG CGA GGC TAC TGC AAT CGC TAC CCG GTG TGC GTG      1846
Cys Asp Gln Cys Gln Arg Gly Tyr Cys Asn Arg Tyr Pro Val Cys Val
        545                 550                 555

GCC TGC CAC CCT TGC TTC CAG ACC TAT GAT GCG GAC CTC CGG GAG CAG      1894
Ala Cys His Pro Cys Phe Gln Thr Tyr Asp Ala Asp Leu Arg Glu Gln
    560                 565                 570

GCC CTG CGC TTT GGT AGA CTC CCG AAT GCC ACC GCC AGC CTG TGG TCA      1942
```

-continued

```
Ala Leu Arg Phe Gly Arg Leu Pro Asn Ala Thr Ala Ser Leu Trp Ser
575                 580                 585                 590

GGG CCT GGG CTG GAG GAC CGT GGC CTG GCC TCC CGG ATC CTA GAT GCA      1990
Gly Pro Gly Leu Glu Asp Arg Gly Leu Ala Ser Arg Ile Leu Asp Ala
                595                 600                 605

AAG AGT AAG ATT GAG CAG ATC CGA GCA GTT CTC AGC AGC CCC GCA GTC      2038
Lys Ser Lys Ile Glu Gln Ile Arg Ala Val Leu Ser Ser Pro Ala Val
            610                 615                 620

ACA GAG CAG GAG GTG GCT CAG GTG GCC AGT GCC ATC CTC TCC CTC AGG      2086
Thr Glu Gln Glu Val Ala Gln Val Ala Ser Ala Ile Leu Ser Leu Arg
        625                 630                 635

CGA ACT CTC CAG GGC CTG CAG CTG GAT CTG CCC CTG GAG GAG GAG ACG      2134
Arg Thr Leu Gln Gly Leu Gln Leu Asp Leu Pro Leu Glu Glu Glu Thr
    640                 645                 650

TTG TCC CTT CCG AGA GAC CTG GAG AGT CTT GAC AGA AGC TTC AAT GGT      2182
Leu Ser Leu Pro Arg Asp Leu Glu Ser Leu Asp Arg Ser Phe Asn Gly
655                 660                 665                 670

CTC CTT ACT ATG TAT CAG AGG AAG AGG GAG CAG TTT GAA AAA ATA AGC      2230
Leu Leu Thr Met Tyr Gln Arg Lys Arg Glu Gln Phe Glu Lys Ile Ser
                675                 680                 685

AGT GCT GAT CCT TCA GGA GCC TTC CGG ATG CTG AGC ACA GCC TAC GAG      2278
Ser Ala Asp Pro Ser Gly Ala Phe Arg Met Leu Ser Thr Ala Tyr Glu
            690                 695                 700

CAG TCA GCC CAG GCT GCT CAG CAG GTC TCC GAC AGC TCG CGC CTT TTG      2326
Gln Ser Ala Gln Ala Ala Gln Gln Val Ser Asp Ser Ser Arg Leu Leu
        705                 710                 715

GAC CAG CTC AGG GAC AGC CGG AGA GAG GCA GAG AGG CTG GTG CGG CAG      2374
Asp Gln Leu Arg Asp Ser Arg Arg Glu Ala Glu Arg Leu Val Arg Gln
    720                 725                 730

GCG GGA GGA GGA GGA GGC ACC GGC AGC CCC AAG CTT GTG GCC CTG AGG      2422
Ala Gly Gly Gly Gly Gly Thr Gly Ser Pro Lys Leu Val Ala Leu Arg
735                 740                 745                 750

TTG GAG ATG TCT TCG TTG CCT GAC CTG ACA CCC ACC TTC AAC AAG CTC      2470
Leu Glu Met Ser Ser Leu Pro Asp Leu Thr Pro Thr Phe Asn Lys Leu
                755                 760                 765

TGT GGC AAC TCC AGG CAG ATG GCT TGC ACC CCA ATA TCA TGC CCT GGT      2518
Cys Gly Asn Ser Arg Gln Met Ala Cys Thr Pro Ile Ser Cys Pro Gly
            770                 775                 780

GAG CTA TGT CCC CAA GAC AAT GGC ACA GCC TGT GCG TCC CGC TGC AGG      2566
Glu Leu Cys Pro Gln Asp Asn Gly Thr Ala Cys Ala Ser Arg Cys Arg
        785                 790                 795

GGT GTC CTT CCC AGG GCC GGT GGG GCC TTC TTG ATG GCG GGG CAG GTG      2614
Gly Val Leu Pro Arg Ala Gly Gly Ala Phe Leu Met Ala Gly Gln Val
    800                 805                 810

GCT GAG CAG CTG CGG GCT TCA ATG CCA GCT CCA GCG ACC AGG CAG ATG      2662
Ala Glu Gln Leu Arg Ala Ser Met Pro Ala Pro Ala Thr Arg Gln Met
815                 820                 825                 830

ATT AGG GCA GCC GAG GAA TCT GCC TCA CAG ATT CAA TCC AGT GCC CAG      2710
Ile Arg Ala Ala Glu Glu Ser Ala Ser Gln Ile Gln Ser Ser Ala Gln
                835                 840                 845

CGC TTG GAG ACC CAG GTG AGC GCC AGC CGC TCC CAG ATG GAG GAA GAT      2758
Arg Leu Glu Thr Gln Val Ser Ala Ser Arg Ser Gln Met Glu Glu Asp
            850                 855                 860

GTC AGA CGC ACA CGG CTC CTA ATC CAG CAG GTC CGG GAC TTC CTA ACA      2806
Val Arg Arg Thr Arg Leu Leu Ile Gln Gln Val Arg Asp Phe Leu Thr
        865                 870                 875

GAC CCC GAC ACT GAT GCA GCC ACT ATC CAG GAG GTC AGG CGA GCC GTG      2854
Asp Pro Asp Thr Asp Ala Ala Thr Ile Gln Glu Val Arg Arg Ala Val
    880                 885                 890

CTG GCC CTG TGG CTG CCC ACA GAC TCA GCT ACT GTT CTG CAG AAG ATG      2902
```

-continued

```
Leu Ala Leu Trp Leu Pro Thr Asp Ser Ala Thr Val Leu Gln Lys Met
895                 900                 905                 910

AAT GAG ATC CAG GCC ATT GCA GCC AGG CTC CCC AAC GTG GAC TTG GTG     2950
Asn Glu Ile Gln Ala Ile Ala Ala Arg Leu Pro Asn Val Asp Leu Val
                915                 920                 925

CTG TCC CAG ACC AAG CAG GAC ATT GGC GGT GCC CGC CGG TTG CAG GCT     2998
Leu Ser Gln Thr Lys Gln Asp Ile Gly Gly Ala Arg Arg Leu Gln Ala
            930                 935                 940

GAG GCT GAG GAA GCC AGG AGC CGA GCC CAT GCA GTG GAG GGC CAG GTG     3046
Glu Ala Glu Glu Ala Arg Ser Arg Ala His Ala Val Glu Gly Gln Val
        945                 950                 955

GAG GAT GTG GTT GGG AAC CTG CGG CAG GGG ACA GTG GCA CTG CAG GAA     3094
Glu Asp Val Val Gly Asn Leu Arg Gln Gly Thr Val Ala Leu Gln Glu
    960                 965                 970

GCT CAG GAC ACC ATG CAA GGC ACC AGC CGG TCC CTT CGG CTT ATC CAG     3142
Ala Gln Asp Thr Met Gln Gly Thr Ser Arg Ser Leu Arg Leu Ile Gln
975                 980                 985                 990

GAC AGG GTT GCT GAG GTT CAG CAG GTA CTC GGC CAG CAA AAG CTG GTG     3190
Asp Arg Val Ala Glu Val Gln Gln Val Leu Gly Gln Gln Lys Leu Val
                995                1000                1005

ACA AGC ATG ACC AAG CAG CTG GGT GAC TTC TGG ACA CGG ATG GAG GAG     3238
Thr Ser Met Thr Lys Gln Leu Gly Asp Phe Trp Thr Arg Met Glu Glu
           1010                1015                1020

CTC CGC CAC CAA GCC CGG CAG CAG GGG GCA GAG GCA GTC CAG GCC CAG     3286
Leu Arg His Gln Ala Arg Gln Gln Gly Ala Glu Ala Val Gln Ala Gln
       1025                1030                1035

CAG CTT GCG GAA GGT GCC AGC GAG CAG GCA TTG AGT GCC CAA GAG GGA     3334
Gln Leu Ala Glu Gly Ala Ser Glu Gln Ala Leu Ser Ala Gln Glu Gly
   1040                1045                1050

TTT GAG AGA ATA AAA CAA AAG TAT GCT GAG TTG AAG GAC CGG TTG GGT     3382
Phe Glu Arg Ile Lys Gln Lys Tyr Ala Glu Leu Lys Asp Arg Leu Gly
1055                1060                1065                1070

CAG AGT TCC ATG CTG GGT GAG CAG GGT GCC CGG ATC CAG AGT GTG AAG     3430
Gln Ser Ser Met Leu Gly Glu Gln Gly Ala Arg Ile Gln Ser Val Lys
               1075                1080                1085

ACA GAG GCA GAG GAG CTG TTT GGG GAG ACC ATG GAG ATG ATG GAC AGG     3478
Thr Glu Ala Glu Glu Leu Phe Gly Glu Thr Met Glu Met Met Asp Arg
           1090                1095                1100

ATG AAA GAC ATG GAG TTG GAG CTG CTG CGG GCA GCA GGC CAT CAT GCT     3526
Met Lys Asp Met Glu Leu Glu Leu Leu Arg Ala Ala Gly His His Ala
       1105                1110                1115

GCG CTC AGC GAC CTG ACA GGA CTG GAG AAG CGT GTG GAG CAG ATC CGT     3574
Ala Leu Ser Asp Leu Thr Gly Leu Glu Lys Arg Val Glu Gln Ile Arg
   1120                1125                1130

GAC CAC ATC AAT GGG CGC GTG CTC TAC TAT GCC ACC TGC AAG T           3617
Asp His Ile Asn Gly Arg Val Leu Tyr Tyr Ala Thr Cys Lys
1135                1140                1145

GATGCTACAC GTTCCAGCCC GTTGCCCCAC TCATCTGCGC GCTTTGCTTT TGGTTGGGGG   3677

GCAGATTGGG TTGGAATGCT TTCCATCTCC AGGAGACTTT CATGTAGCCC AAAGTACAGC   3737

CTGGACCACC CCTGGTGTGA GTAGCTAGTA AGATTACCCT GAGCTGCAGC TGAGCCTGAG   3797

CCAATGGGAC AGTTACACTT GACAGACAAA GATGGTGGAG ATTGGCATGC CATTGAAACT   3857

AAGAGCTCTC AAGTCAAGGA AGCTGGGCTG GGCAGTATCC CCCGCCTTTA GTTCTCCACA   3917

AAAAAAAAAA AAAA                                                     3931
```

(2) INFORMATION FOR SEQ ID NO:2:

(i) SEQUENCE CHARACTERISTICS:
(A) LENGTH: 1165 amino acids (B) TYPE: amino acid
(D) TOPOLOGY: linear (ii) MOLECULE TYPE: protein (xi) SEQUENCE DESCRIPTION: SEQ ID NO:2:

```
Met Arg Pro Phe Phe Leu Leu Cys Phe Ala Leu Pro Gly Leu Leu His
-17     -15                 -10                 -5

Ala Gln Gln Ala Cys Ser Arg Gly Ala Cys Tyr Pro Pro Val Gly Asp
      1               5                  10                  15

Leu Leu Val Gly Arg Thr Arg Phe Leu Arg Ala Ser Ser Thr Cys Gly
                 20                  25                  30

Leu Thr Lys Pro Glu Thr Tyr Cys Thr Gln Tyr Gly Glu Trp Gln Met
             35                  40                  45

Lys Cys Cys Lys Cys Asp Ser Arg Gln Pro His Asn Tyr Tyr Ser His
         50                  55                  60

Arg Val Glu Asn Val Ala Ser Ser Ser Gly Pro Met Arg Trp Trp Gln
     65                  70                  75

Ser Gln Asn Asp Val Asn Pro Val Ser Leu Gln Leu Asp Leu Asp Arg
 80                  85                  90                  95

Arg Phe Gln Leu Gln Glu Val Met Met Glu Phe Pro Gly Ala His Ala
                100                 105                 110

Ala Gly Met Leu Ile Glu Arg Ser Ser Asp Phe Gly Lys Thr Trp Arg
            115                 120                 125

Val Tyr Gln Tyr Leu Ala Ala Asp Cys Thr Ser Thr Phe Pro Arg Val
        130                 135                 140

Arg Gln Gly Arg Pro Gln Ser Trp Gln Asp Val Arg Cys Gln Ser Leu
    145                 150                 155

Pro Gln Arg Pro Asn Ala Arg Leu Asn Gly Gly Lys Val Gln Leu Asn
160                 165                 170                 175

Leu Met Asp Leu Val Ser Gly Ile Pro Ala Thr Gln Ser Gln Lys Ile
                180                 185                 190

Gln Glu Val Gly Glu Ile Thr Asn Leu Arg Val Asn Phe Thr Arg Leu
            195                 200                 205

Ala Pro Val Pro Lys Leu Asp His Pro Pro Ser Ala Tyr Tyr Ala Val
        210                 215                 220

Ser Gln Leu Arg Leu Gln Gly Ser Cys Phe Cys His Gly His Ala Asp
    225                 230                 235

Arg Cys Ala Pro Lys Pro Gly Ala Ser Ala Gly Ser Thr Ala Val Gln
240                 245                 250                 255

Val His Asp Val Cys Val Cys Gln His Asn Thr Ala Gly Pro Asn Cys
                260                 265                 270

Glu Arg Cys Ala Pro Phe Tyr Asn Asn Arg Pro Trp Arg Pro Ala Glu
            275                 280                 285

Gly Gln Asp Ala His Glu Cys Gln Arg Cys Asp Cys Asn Gly His Ser
        290                 295                 300

Glu Asn Cys His Phe Asp Pro Ala Val Phe Ala Ala Ser Gln Gly Ala
    305                 310                 315

Tyr Gly Gly Val Cys Asp Asn Cys Arg Asp His Thr Glu Gly Lys Asn
320                 325                 330                 335

Cys Glu Arg Cys Gln Leu His Tyr Phe Arg Asn Arg Arg Pro Gly Ala
                340                 345                 350

Ser Ile Gln Glu Thr Cys Ile Ser Cys Glu Cys Asp Pro Asp Gly Gln
            355                 360                 365

Trp Ala Gly Ala Pro Cys Asp Pro Val Thr Gly Gln Cys Val Cys Lys
```

-continued

```
        370                 375                 380

Glu His Val Gln Gly Glu Arg Cys Asp Leu Cys Lys Pro Gly Phe Thr
    385                 390                 395

Gly Leu Thr Tyr Ala Asn Pro Gln Gly Cys His Arg Cys Asp Cys Asn
400                 405                 410                 415

Ile Leu Pro Ser Arg Arg Leu Pro Cys Asp Glu Glu Ser Gly Arg Cys
                420                 425                 430

Leu Cys Leu Pro Asn Val Gly Gly Pro Lys Cys Asp Gln Cys Ala Pro
            435                 440                 445

Tyr His Trp Lys Leu Ala Ser Gly Gln Gly Cys Glu Pro Cys Ala Cys
        450                 455                 460

Asp Pro His Asn Ser Leu Ser Pro Gln Cys Asn Gln Phe Thr Gly Gln
    465                 470                 475

Cys Pro Cys Arg Glu Gly Phe Gly Gly Leu Met Cys Ser Ala Ala Ala
480                 485                 490                 495

Ile Arg Gln Cys Pro Asp Arg Thr Tyr Gly Asp Val Ala Thr Gly Cys
                500                 505                 510

Arg Ala Cys Asp Cys Asp Phe Arg Gly Thr Glu Gly Pro Gly Cys Asp
            515                 520                 525

Lys Ala Ser Gly Val Leu Cys Arg Pro Gly Leu Thr Gly Pro Arg Cys
        530                 535                 540

Asp Gln Cys Gln Arg Gly Tyr Cys Asn Arg Tyr Pro Val Cys Val Ala
    545                 550                 555

Cys His Pro Cys Phe Gln Thr Tyr Asp Ala Asp Leu Arg Glu Gln Ala
560                 565                 570                 575

Leu Arg Phe Gly Arg Leu Pro Asn Ala Thr Ala Ser Leu Trp Ser Gly
                580                 585                 590

Pro Gly Leu Glu Asp Arg Gly Leu Ala Ser Arg Ile Leu Asp Ala Lys
            595                 600                 605

Ser Lys Ile Glu Gln Ile Arg Ala Val Leu Ser Ser Pro Ala Val Thr
        610                 615                 620

Glu Gln Glu Val Ala Gln Val Ala Ser Ala Ile Leu Ser Leu Arg Arg
    625                 630                 635

Thr Leu Gln Gly Leu Gln Leu Asp Leu Pro Leu Glu Glu Glu Thr Leu
640                 645                 650                 655

Ser Leu Pro Arg Asp Leu Glu Ser Leu Asp Arg Ser Phe Asn Gly Leu
                660                 665                 670

Leu Thr Met Tyr Gln Arg Lys Arg Glu Gln Phe Glu Lys Ile Ser Ser
            675                 680                 685

Ala Asp Pro Ser Gly Ala Phe Arg Met Leu Ser Thr Ala Tyr Glu Gln
        690                 695                 700

Ser Ala Gln Ala Ala Gln Gln Val Ser Asp Ser Ser Arg Leu Leu Asp
    705                 710                 715

Gln Leu Arg Asp Ser Arg Arg Glu Ala Glu Arg Leu Val Arg Gln Ala
720                 725                 730                 735

Gly Gly Gly Gly Gly Thr Gly Ser Pro Lys Leu Val Ala Leu Arg Leu
                740                 745                 750

Glu Met Ser Ser Leu Pro Asp Leu Thr Pro Thr Phe Asn Lys Leu Cys
            755                 760                 765

Gly Asn Ser Arg Gln Met Ala Cys Thr Pro Ile Ser Cys Pro Gly Glu
        770                 775                 780

Leu Cys Pro Gln Asp Asn Gly Thr Ala Cys Ala Ser Arg Cys Arg Gly
    785                 790                 795
```

-continued

```
Val Leu Pro Arg Ala Gly Gly Ala Phe Leu Met Ala Gly Gln Val Ala
800                 805                 810                 815

Glu Gln Leu Arg Ala Ser Met Pro Ala Pro Ala Thr Arg Gln Met Ile
                820                 825                 830

Arg Ala Ala Glu Glu Ser Ala Ser Gln Ile Gln Ser Ser Ala Gln Arg
            835                 840                 845

Leu Glu Thr Gln Val Ser Ala Ser Arg Ser Gln Met Glu Glu Asp Val
        850                 855                 860

Arg Arg Thr Arg Leu Leu Ile Gln Gln Val Arg Asp Phe Leu Thr Asp
    865                 870                 875

Pro Asp Thr Asp Ala Ala Thr Ile Gln Glu Val Arg Arg Ala Val Leu
880                 885                 890                 895

Ala Leu Trp Leu Pro Thr Asp Ser Ala Thr Val Leu Gln Lys Met Asn
                900                 905                 910

Glu Ile Gln Ala Ile Ala Ala Arg Leu Pro Asn Val Asp Leu Val Leu
            915                 920                 925

Ser Gln Thr Lys Gln Asp Ile Gly Gly Ala Arg Arg Leu Gln Ala Glu
        930                 935                 940

Ala Glu Glu Ala Arg Ser Arg Ala His Ala Val Glu Gly Gln Val Glu
    945                 950                 955

Asp Val Val Gly Asn Leu Arg Gln Gly Thr Val Ala Leu Gln Glu Ala
960                 965                 970                 975

Gln Asp Thr Met Gln Gly Thr Ser Arg Ser Leu Arg Leu Ile Gln Asp
                980                 985                 990

Arg Val Ala Glu Val Gln Gln Val Leu Gly Gln Gln Lys Leu Val Thr
            995                 1000                1005

Ser Met Thr Lys Gln Leu Gly Asp Phe Trp Thr Arg Met Glu Glu Leu
        1010                1015                1020

Arg His Gln Ala Arg Gln Gln Gly Ala Glu Ala Val Gln Ala Gln Gln
    1025                1030                1035

Leu Ala Glu Gly Ala Ser Glu Gln Ala Leu Ser Ala Gln Glu Gly Phe
1040                1045                1050                1055

Glu Arg Ile Lys Gln Lys Tyr Ala Glu Leu Lys Asp Arg Leu Gly Gln
                1060                1065                1070

Ser Ser Met Leu Gly Glu Gln Gly Ala Arg Ile Gln Ser Val Lys Thr
            1075                1080                1085

Glu Ala Glu Glu Leu Phe Gly Glu Thr Met Glu Met Met Asp Arg Met
        1090                1095                1100

Lys Asp Met Glu Leu Glu Leu Leu Arg Ala Ala Gly His His Ala Ala
    1105                1110                1115

Leu Ser Asp Leu Thr Gly Leu Glu Lys Arg Val Glu Gln Ile Arg Asp
1120                1125                1130                1135

His Ile Asn Gly Arg Val Leu Tyr Tyr Ala Thr Cys Lys
                1140                1145
```

(2) INFORMATION FOR SEQ ID NO:3:

(i) SEQUENCE CHARACTERISTICS:
(A) LENGTH: 1147 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Domain (B) LOCATION: 1..231

(ix) FEATURE:
(A) NAME/KEY: Domain
(B) LOCATION: 232..411

(ix) FEATURE:
(A) NAME/KEY: Domain
(B) LOCATION: 412..765

(ix) FEATURE:
(A) NAME/KEY: Domain
(B) LOCATION: 766..1147

(xi) SEQUENCE DESCRIPTION: SEQ ID NO:3:

```
Gln Gln Ala Cys Ser Arg Gly Ala Cys Tyr Pro Pro Val Gly Asp Leu
1               5                   10                  15

Leu Val Gly Arg Thr Arg Phe Leu Arg Ala Ser Ser Thr Cys Gly Leu
            20                  25                  30

Thr Lys Pro Glu Thr Tyr Cys Thr Gln Tyr Gly Glu Trp Gln Met Lys
        35                  40                  45

Cys Cys Lys Cys Asp Ser Arg Gln Pro His Asn Tyr Tyr Ser His Arg
    50                  55                  60

Val Glu Asn Val Ala Ser Ser Ser Gly Pro Met Arg Trp Trp Gln Ser
65                  70                  75                  80

Gln Asn Asp Val Asn Pro Val Ser Leu Gln Leu Asp Leu Asp Arg Arg
                85                  90                  95

Phe Gln Leu Gln Glu Val Met Met Glu Phe Pro Gly Ala His Ala Ala
            100                 105                 110

Gly Met Leu Ile Glu Arg Ser Ser Asp Phe Gly Lys Thr Trp Arg Val
        115                 120                 125

Tyr Gln Tyr Leu Ala Ala Asp Cys Thr Ser Thr Phe Pro Arg Val Arg
    130                 135                 140

Gln Gly Arg Pro Gln Ser Trp Gln Asp Val Arg Cys Gln Ser Leu Pro
145                 150                 155                 160

Gln Arg Pro Asn Ala Arg Leu Asn Gly Gly Lys Val Gln Leu Asn Leu
                165                 170                 175

Met Asp Leu Val Ser Gly Ile Pro Ala Thr Gln Ser Gln Lys Ile Gln
            180                 185                 190

Glu Val Gly Glu Ile Thr Asn Leu Arg Val Asn Phe Thr Arg Leu Ala
        195                 200                 205

Pro Val Pro Lys Leu Asp His Pro Pro Ser Ala Tyr Tyr Ala Val Ser
    210                 215                 220

Gln Leu Arg Leu Gln Gly Ser Cys Phe Cys His Gly His Ala Asp Arg
225                 230                 235                 240

Cys Ala Pro Lys Pro Gly Ala Ser Ala Gly Ser Thr Ala Val Gln Val
                245                 250                 255

His Asp Val Cys Val Cys Gln His Asn Thr Ala Gly Pro Asn Cys Glu
            260                 265                 270

Arg Cys Ala Pro Phe Tyr Asn Asn Arg Pro Trp Arg Pro Ala Glu Gly
        275                 280                 285

Gln Asp Ala His Glu Cys Gln Arg Cys Asp Cys Asn Gly His Ser Glu
    290                 295                 300

Asn Cys His Phe Asp Pro Ala Val Phe Ala Ala Ser Gln Gly Ala Tyr
305                 310                 315                 320

Gly Gly Val Cys Asp Asn Cys Arg Asp His Thr Glu Gly Lys Asn Cys
                325                 330                 335

Glu Arg Cys Gln Leu His Tyr Phe Arg Asn Arg Arg Pro Gly Ala Ser
```

-continued

```
            340                 345                 350

Ile Gln Glu Thr Cys Ile Ser Cys Glu Cys Asp Pro Asp Gly Gln Trp
        355                 360                 365

Ala Gly Ala Pro Cys Asp Pro Val Thr Gly Gln Cys Val Cys Lys Glu
    370                 375                 380

His Val Gln Gly Glu Arg Cys Asp Leu Cys Lys Pro Gly Phe Thr Gly
385                 390                 395                 400

Leu Thr Tyr Ala Asn Pro Gln Gly Cys His Arg Cys Asp Cys Asn Ile
                405                 410                 415

Leu Pro Ser Arg Arg Leu Pro Cys Asp Glu Glu Ser Gly Arg Cys Leu
            420                 425                 430

Cys Leu Pro Asn Val Gly Gly Pro Lys Cys Asp Gln Cys Ala Pro Tyr
        435                 440                 445

His Trp Lys Leu Ala Ser Gly Gln Gly Cys Glu Pro Cys Ala Cys Asp
    450                 455                 460

Pro His Asn Ser Leu Ser Pro Gln Cys Asn Gln Phe Thr Gly Gln Cys
465                 470                 475                 480

Pro Cys Arg Glu Gly Phe Gly Gly Leu Met Cys Ser Ala Ala Ala Ile
                485                 490                 495

Arg Gln Cys Pro Asp Arg Thr Tyr Gly Asp Val Ala Thr Gly Cys Arg
            500                 505                 510

Ala Cys Asp Cys Asp Phe Arg Gly Thr Glu Gly Pro Gly Cys Asp Lys
        515                 520                 525

Ala Ser Gly Val Leu Cys Arg Pro Gly Leu Thr Gly Pro Arg Cys Asp
    530                 535                 540

Gln Cys Arg Gly Tyr Cys Asn Arg Tyr Pro Val Cys Val Ala Cys His
545                 550                 555                 560

Pro Cys Phe Gln Thr Tyr Asp Ala Asp Leu Arg Glu Gln Ala Leu Arg
                565                 570                 575

Phe Gly Arg Leu Pro Asn Ala Thr Ala Ser Leu Trp Ser Gly Pro Gly
            580                 585                 590

Leu Glu Asp Arg Gly Leu Ala Ser Arg Ile Leu Asp Ala Lys Ser Lys
        595                 600                 605

Ile Glu Gln Ile Arg Ala Val Leu Ser Ser Pro Ala Val Thr Glu Gln
    610                 615                 620

Glu Val Ala Gln Val Ala Ser Ala Ile Leu Ser Leu Arg Arg Thr Leu
625                 630                 635                 640

Gln Gly Leu Gln Leu Asp Leu Pro Leu Glu Glu Glu Thr Leu Ser Leu
                645                 650                 655

Pro Arg Asp Leu Glu Ser Leu Asp Arg Ser Phe Asn Gly Leu Leu Thr
            660                 665                 670

Met Tyr Gln Arg Lys Arg Glu Gln Phe Glu Lys Ile Ser Ser Ala Asp
        675                 680                 685

Pro Ser Gly Ala Phe Arg Met Leu Ser Thr Ala Tyr Glu Gln Ser Ala
    690                 695                 700

Gln Ala Ala Gln Gln Val Ser Asp Ser Ser Arg Leu Leu Asp Gln Leu
705                 710                 715                 720

Arg Asp Ser Arg Arg Glu Ala Glu Arg Leu Val Arg Gln Ala Gly Gly
                725                 730                 735

Gly Gly Gly Thr Gly Ser Pro Lys Leu Val Ala Leu Arg Leu Glu Met
            740                 745                 750

Ser Ser Leu Pro Asp Leu Thr Pro Thr Phe Asn Lys Leu Cys Gly Asn
        755                 760                 765
```

-continued

```
Ser Arg Gln Met Ala Cys Thr Pro Ile Ser Cys Pro Gly Glu Leu Cys
    770                 775                 780

Pro Gln Asp Asn Gly Thr Ala Cys Ala Ser Arg Cys Arg Gly Val Leu
785                 790                 795                 800

Pro Arg Ala Gly Gly Ala Phe Leu Met Ala Gly Gln Val Ala Glu Gln
                805                 810                 815

Leu Arg Ala Ser Met Pro Ala Pro Ala Thr Arg Gln Met Ile Arg Ala
            820                 825                 830

Ala Glu Glu Ser Ala Ser Gln Ile Gln Ser Ser Ala Gln Arg Leu Glu
        835                 840                 845

Thr Gln Val Ser Ala Ser Arg Ser Gln Met Glu Glu Asp Val Arg Arg
    850                 855                 860

Thr Arg Leu Leu Ile Gln Gln Val Arg Asp Phe Leu Thr Asp Pro Asp
865                 870                 875                 880

Thr Asp Ala Ala Thr Ile Gln Glu Val Arg Arg Ala Val Leu Ala Leu
                885                 890                 895

Trp Leu Pro Thr Asp Ser Ala Thr Val Leu Gln Lys Met Asn Glu Ile
            900                 905                 910

Gln Ala Ile Ala Ala Arg Leu Pro Asn Val Asp Leu Val Leu Ser Gln
        915                 920                 925

Thr Lys Gln Asp Ile Gly Gly Ala Arg Arg Leu Gln Ala Glu Ala Glu
    930                 935                 940

Glu Ala Arg Ser Arg Ala His Ala Val Glu Gly Gln Val Glu Asp Val
945                 950                 955                 960

Val Gly Asn Leu Arg Gln Gly Thr Val Ala Leu Gln Glu Ala Gln Asp
                965                 970                 975

Thr Met Gln Gly Thr Ser Arg Ser Leu Arg Leu Ile Gln Asp Arg Val
            980                 985                 990

Ala Glu Val Gln Gln Val Leu Gly Gln Gln Lys Leu Val Thr Ser Met
        995                 1000                1005

Thr Lys Gln Leu Gly Asp Phe Trp Thr Arg Met Glu Glu Leu Arg His
    1010                1015                1020

Gln Ala Arg Gln Gln Gly Ala Glu Ala Val Gln Ala Gln Gln Leu Ala
1025                1030                1035                1040

Glu Gly Ala Ser Glu Gln Ala Leu Ser Ala Gln Glu Gly Phe Glu Arg
                1045                1050                1055

Ile Lys Gln Lys Tyr Ala Glu Leu Lys Asp Arg Leu Gly Gln Ser Ser
            1060                1065                1070

Met Leu Gly Glu Gln Gly Ala Arg Ile Gln Ser Val Lys Thr Glu Ala
        1075                1080                1085

Glu Glu Leu Phe Gly Glu Thr Met Glu Met Met Asp Arg Met Lys Asp
    1090                1095                1100

Met Glu Leu Glu Leu Leu Arg Ala Ala Gly His His Ala Ala Leu Ser
1105                1110                1115                1120

Asp Leu Thr Gly Leu Glu Lys Arg Val Glu Gln Ile Arg Asp His Ile
                1125                1130                1135

Asn Gly Arg Val Leu Tyr Tyr Ser Thr Cys Lys
            1140                1145
```

(2) INFORMATION FOR SEQ ID NO:4:

(i) SEQUENCE CHARACTERISTICS:
(A) LENGTH: 1196 amino acids
(B) TYPE: amino acid
(D) TOPOLOGY: linear (ii) MOLECULE TYPE: peptide (v) FRAGMENT TYPE: internal (ix) FEATURE:
(A) NAME/KEY: Domain
(B) LOCATION: 1..250

(ix) FEATURE:
(A) NAME/KEY: Domain
(B) LOCATION: 251..437

(ix) FEATURE:
(A) NAME/KEY: Domain
(B) LOCATION: 438..807

(ix) FEATURE:
(A) NAME/KEY: Domain
(B) LOCATION: 808..840

(ix) FEATURE:
(A) NAME/KEY: Domain
(B) LOCATION: 841..1196

(xi) SEQUENCE DESCRIPTION: SEQ ID NO:4:

```
Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20                  25                  30

Ser Thr Thr Cys Gly Leu His Lys Pro Glu Pro Tyr Cys Ile Val Ser
        35                  40                  45

His Leu Gln Glu Asp Lys Lys Cys Phe Ile Cys Asn Ser Gln Asp Pro
    50                  55                  60

Tyr His Glu Thr Leu Asn Pro Asp Ser His Leu Ile Glu Asn Val Val
65                  70                  75                  80

Thr Thr Phe Ala Pro Asn Arg Leu Lys Ile Trp Trp Gln Ser Glu Asn
                85                  90                  95

Gly Val Glu Asn Val Thr Ile Gln Leu Asp Leu Glu Ala Glu Phe His
            100                 105                 110

Phe Thr His Leu Ile Met Thr Phe Lys Thr Phe Arg Pro Ala Ala Met
        115                 120                 125

Leu Ile Glu Arg Ser Ser Asp Phe Gly Lys Thr Trp Gly Val Tyr Arg
    130                 135                 140

Tyr Phe Ala Tyr Asp Cys Glu Ala Ser Phe Pro Gly Ile Ser Thr Gly
145                 150                 155                 160

Pro Met Lys Lys Val Asp Asp Ile Ile Cys Asp Ser Arg Tyr Ser Asp
                165                 170                 175

Ile Glu Pro Ser Thr Glu Gly Glu Val Ile Phe Arg Ala Leu Asp Pro
            180                 185                 190

Ala Phe Lys Ile Glu Asp Pro Tyr Ser Pro Arg Ile Gln Asn Leu Leu
        195                 200                 205

Lys Ile Thr Asn Leu Arg Ile Lys Phe Val Lys Leu His Thr Leu Gly
    210                 215                 220

Asp Asn Leu Leu Asp Ser Arg Met Glu Ile Arg Glu Lys Tyr Tyr Tyr
225                 230                 235                 240

Ala Val Tyr Asp Met Val Val Arg Gly Asn Cys Phe Cys Tyr Gly His
                245                 250                 255

Ala Ser Glu Cys Ala Pro Val Asp Gly Phe Asn Glu Glu Val Glu Gly
            260                 265                 270

Met Val His Gly His Cys Met Cys Arg His Asn Thr Lys Gly Leu Asn
        275                 280                 285
```

-continued

```
Cys Glu Leu Cys Met Asp Phe Tyr His Asp Leu Pro Trp Arg Pro Ala
    290                 295                 300

Glu Gly Arg Asn Ser Asn Ala Cys Lys Lys Cys Asn Cys Asn Glu His
305                 310                 315                 320

Ser Ile Ser Cys His Phe Asp Met Ala Val Tyr Leu Ala Thr Gly Asn
                325                 330                 335

Val Ser Gly Gly Val Cys Asp Asp Cys Gln His Asn Thr Met Gly Arg
            340                 345                 350

Asn Cys Glu Gln Cys Lys Pro Phe Tyr Tyr Gln His Pro Glu Arg Asp
        355                 360                 365

Ile Arg Asp Pro Asn Phe Cys Glu Arg Cys Thr Cys Asp Pro Ala Gly
    370                 375                 380

Ser Gln Asn Glu Gly Ile Cys Asp Ser Tyr Thr Asp Phe Ser Thr Gly
385                 390                 395                 400

Leu Ile Ala Gly Gln Cys Arg Cys Lys Leu Asn Val Glu Gly Glu His
                405                 410                 415

Cys Asp Val Cys Lys Glu Gly Phe Tyr Asp Leu Ser Ser Glu Asp Pro
            420                 425                 430

Phe Gly Cys Lys Ser Cys Val Cys Asn Tyr Leu Gly Thr Val Gln Glu
        435                 440                 445

His Cys Asn Gly Ser Asp Cys Gln Cys Asp Lys Ala Thr Gly Gln Cys
    450                 455                 460

Leu Cys Leu Pro Asn Val Ile Gly Gln Asn Cys Asp Arg Cys Ala Pro
465                 470                 475                 480

Asn Thr Trp Gln Leu Ala Ser Gly Thr Gly Cys Asp Pro Cys Asn Cys
                485                 490                 495

Asn Ala Ala His Ser Phe Gly Pro Ser Cys Asn Glu Phe Thr Gly Gln
            500                 505                 510

Cys Gln Cys Met Pro Gly Phe Gly Gly Arg Thr Cys Ser Glu Cys Gln
        515                 520                 525

Glu Leu Phe Trp Gly Asp Pro Asp Val Glu Cys Arg Ala Cys Asp Cys
    530                 535                 540

Asp Pro Arg Gly Ile Glu Thr Pro Gln Cys Asp Gln Ser Thr Gly Gln
545                 550                 555                 560

Cys Val Cys Val Glu Gly Val Glu Gly Pro Arg Cys Asp Lys Cys Thr
                565                 570                 575

Arg Gly Tyr Ser Gly Val Phe Pro Asp Cys Thr Pro Cys His Gln Cys
            580                 585                 590

Phe Ala Leu Trp Asp Val Ile Ile Ala Glu Leu Thr Asn Arg Thr His
        595                 600                 605

Arg Phe Leu Glu Lys Ala Lys Ala Leu Lys Ile Ser Gly Val Ile Gly
    610                 615                 620

Pro Tyr Arg Glu Thr Val Asp Ser Val Glu Arg Lys Val Ser Glu Ile
625                 630                 635                 640

Lys Asp Ile Leu Ala Gln Ser Pro Ala Ala Glu Pro Leu Lys Asn Ile
                645                 650                 655

Gly Asn Leu Phe Glu Glu Ala Glu Lys Leu Ile Lys Asp Val Thr Glu
            660                 665                 670

Met Met Ala Gln Val Glu Val Lys Leu Ser Asp Thr Thr Ser Gln Ser
        675                 680                 685

Asn Ser Thr Ala Lys Glu Leu Asp Ser Leu Gln Thr Glu Ala Glu Ser
    690                 695                 700

Leu Asp Asn Thr Val Lys Glu Leu Ala Glu Gln Leu Glu Phe Ile Lys
705                 710                 715                 720
```

-continued

```
Asn Ser Asp Ile Arg Gly Ala Leu Asp Ser Ile Thr Lys Tyr Phe Gln
            725                 730                 735

Met Ser Leu Glu Ala Glu Glu Arg Val Asn Ala Ser Thr Thr Glu Pro
        740                 745                 750

Asn Ser Thr Val Glu Gln Ser Ala Leu Met Arg Asp Arg Val Glu Asp
    755                 760                 765

Val Met Met Glu Arg Glu Ser Gln Phe Lys Glu Lys Gln Glu Glu Gln
770                 775                 780

Ala Arg Leu Leu Asp Glu Leu Ala Gly Lys Leu Gln Ser Leu Asp Leu
785                 790                 795                 800

Ser Ala Ala Ala Glu Met Thr Cys Gly Thr Pro Pro Gly Ala Ser Cys
            805                 810                 815

Ser Glu Thr Glu Cys Gly Gly Pro Asn Cys Arg Thr Asp Glu Gly Glu
        820                 825                 830

Arg Lys Cys Gly Gly Pro Gly Cys Gly Gly Leu Val Thr Val Ala His
    835                 840                 845

Asn Ala Trp Gln Lys Ala Met Asp Leu Asp Gln Asp Val Leu Ser Ala
850                 855                 860

Leu Ala Glu Val Glu Gln Leu Ser Lys Met Val Ser Glu Ala Lys Leu
865                 870                 875                 880

Arg Ala Asp Glu Ala Lys Gln Ser Ala Glu Asp Ile Leu Leu Lys Thr
            885                 890                 895

Asn Ala Thr Lys Glu Lys Met Asp Lys Ser Asn Glu Glu Leu Arg Asn
        900                 905                 910

Leu Ile Lys Gln Ile Arg Asn Phe Leu Thr Gln Asp Ser Ala Asp Leu
    915                 920                 925

Asp Ser Ile Glu Ala Val Ala Asn Glu Val Leu Lys Met Glu Met Pro
930                 935                 940

Ser Thr Pro Gln Gln Leu Gln Asn Leu Thr Glu Asp Ile Arg Glu Arg
945                 950                 955                 960

Val Glu Ser Leu Ser Gln Val Glu Val Ile Leu Gln His Ser Ala Ala
            965                 970                 975

Asp Ile Ala Arg Ala Glu Met Leu Leu Glu Glu Ala Lys Arg Ala Ser
        980                 985                 990

Lys Ser Ala Thr Asp Val Lys Val Thr Ala Asp Met Val Lys Glu Ala
    995                 1000                1005

Leu Glu Glu Ala Glu Lys Ala Gln Val Ala Ala Glu Lys Ala Ile Lys
    1010                1015                1020

Gln Ala Asp Glu Asp Ile Gln Gly Thr Gln Asn Leu Leu Thr Ser Ile
1025                1030                1035                1040

Glu Ser Glu Thr Ala Ala Ser Glu Glu Thr Leu Phe Asn Ala Ser Gln
            1045                1050                1055

Arg Ile Ser Glu Leu Glu Arg Asn Val Glu Glu Leu Lys Arg Lys Ala
        1060                1065                1070

Ala Gln Asn Ser Gly Glu Ala Glu Tyr Ile Glu Lys Val Val Tyr Thr
    1075                1080                1085

Val Lys Gln Ser Ala Glu Asp Val Lys Lys Thr Leu Asp Gly Glu Leu
    1090                1095                1100

Asp Glu Lys Tyr Lys Lys Val Glu Asn Leu Ile Ala Lys Lys Thr Glu
1105                1110                1115                1120

Glu Ser Ala Asp Ala Arg Arg Lys Ala Glu Met Leu Gln Asn Glu Ala
            1125                1130                1135

Lys Thr Leu Leu Ala Gln Ala Asn Ser Lys Leu Gln Leu Leu Lys Asp
```

-continued 1140 1145 1150

Leu Glu Arg Lys Tyr Glu Asp Asn Gln Arg Tyr Leu Glu Asp Lys Ala
1155 1160 1165

Gln Glu Leu Ala Arg Leu Glu Gly Glu Val Arg Ser Leu Leu Lys Asp
1170 1175 1180

Ile Ser Gln Lys Val Ala Val Tyr Ser Thr Cys Leu
1185 1190 1195

(2) INFORMATION FOR SEQ ID NO:5:

(i) SEQUENCE CHARACTERISTICS:
(A) LENGTH: 231 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:5:

Gln Gln Ala Cys Ser Arg Gly Ala Cys Tyr Pro Pro Val Gly Asp Leu
1 5 10 15

Leu Val Gly Arg Thr Arg Phe Leu Arg Ala Ser Ser Thr Cys Gly Leu
20 25 30

Thr Lys Pro Glu Thr Tyr Cys Thr Gln Tyr Gly Glu Trp Gln Met Lys
35 40 45

Cys Cys Lys Cys Asn Ser Arg Gln Pro His Asn Tyr Tyr Ser His Arg
50 55 60

Val Glu Asn Val Ala Ser Ser Ser Gly Pro Met Arg Trp Trp Gln Ser
65 70 75 80

Gln Asn Asp Val Asn Pro Val Ser Leu Gln Leu Asp Leu Asp Arg Arg
85 90 95

Phe Gln Leu Gln Glu Val Met Met Glu Phe Pro Gly Ala His Ala Ala
100 105 110

Gly Met Leu Ile Glu Arg Ser Ser Asp Phe Gly Lys Thr Trp Arg Val
115 120 125

Tyr Gln Tyr Leu Ala Ala Asp Cys Thr Ser Thr Phe Pro Arg Val Arg
130 135 140

Gln Gly Arg Pro Gln Ser Trp Gln Asp Val Arg Cys Gln Ser Leu Pro
145 150 155 160

Gln Arg Pro Asn Ala Arg Leu Asn Gly Gly Lys Val Gln Leu Asn Leu
165 170 175

Met Asp Leu Val Ser Gly Ile Glu Ala Thr Gln Ser Gln Lys Ile Gln
180 185 190

Glu Val Gly Glu Ile Thr Asn Leu Arg Ile Lys Phe Val Lys Leu Ala
195 200 205

Pro Val Pro Lys Leu Asp His Pro Pro Ser Ala Tyr Tyr Ala Val Ser
210 215 220

Gln Leu Arg Leu Gln Gly Ser
225 230

(2) INFORMATION FOR SEQ ID NO:6:

(i) SEQUENCE CHARACTERISTICS:
(A) LENGTH: 249 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:6:

```
Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20                  25                  30

Ser Thr Cys Gly Leu His Lys Pro Glu Pro Tyr Cys Ile Val Ser His
        35                  40                  45

Leu Gln Glu Asp Lys Lys Cys Phe Ile Cys Asn Ser Gln Asp Pro Tyr
    50                  55                  60

His Glu Thr Leu Asn Pro Asp Ser His Leu Ile Glu Asn Val Val Thr
65                  70                  75                  80

Thr Phe Ala Pro Asn Arg Leu Lys Ile Trp Trp Gln Ser Glu Asn Gly
                85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
    130                 135                 140

Phe Ala Tyr Asp Cys Glu Ala Ser Phe Pro Gly Ile Ser Thr Gly Pro
145                 150                 155                 160

Met Lys Lys Val Asp Asp Ile Ile Cys Asp Ser Arg Tyr Ser Asp Ile
                165                 170                 175

Glu Pro Ser Thr Glu Gly Glu Val Ile Phe Arg Ala Leu Asp Pro Ala
            180                 185                 190

Phe Lys Ile Glu Asp Pro Tyr Ser Pro Arg Ile Gln Asn Leu Leu Lys
        195                 200                 205

Ile Thr Asn Leu Arg Ile Lys Phe Val Lys Leu His Thr Leu Gly Asp
    210                 215                 220

Asn Leu Leu Asp Ser Arg Met Glu Ile Arg Glu Lys Tyr Tyr Tyr Ala
225                 230                 235                 240

Val Tyr Asp Met Val Val Arg Gly Asn
                245
```

(2) INFORMATION FOR SEQ ID NO:7:

(i) SEQUENCE CHARACTERISTICS:
(A) LENGTH: 250 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:7:

```
Gln Val Pro Ser Leu Asp Val Pro Gly Cys Ser Arg Gly Ser Cys Tyr
1               5                   10                  15

Pro Ala Thr Gly Asp Leu Leu Val Gly Arg Ala Asp Arg Leu Thr Ala
            20                  25                  30

Ser Ser Thr Cys Gly Leu His Ser Pro Gln Pro Tyr Cys Ile Val Ser
        35                  40                  45

His Leu Gln Asp Glu Lys Lys Cys Phe Leu Cys Asp Ser Arg Arg Pro
    50                  55                  60

Phe Ser Ala Arg Asp Asn Pro Asn Ser His Arg Ile Gln Asn Val Val
65                  70                  75                  80
```

-continued

Thr Ser Phe Ala Pro Gln Arg Arg Thr Ala Trp Trp Gln Ser Glu Asn
85 90 95

Gly Val Pro Met Val Thr Ile Gln Leu Asp Leu Glu Ala Glu Phe His
100 105 110

Phe Thr His Leu Ile Met Thr Phe Lys Thr Phe Arg Pro Ala Ala Met
115 120 125

Leu Val Glu Arg Ser Ala Asp Phe Gly Arg Thr Trp Arg Val Tyr Arg
130 135 140

Tyr Phe Ser Tyr Asp Cys Gly Ala Asp Phe Pro Gly Ile Pro Leu Ala
145 150 155 160

Pro Pro Arg Arg Trp Asp Asp Val Val Cys Glu Ser Arg Tyr Ser Glu
165 170 175

Ile Glu Pro Ser Thr Glu Gly Glu Val Ile Tyr Arg Val Leu Asp Pro
180 185 190

Ala Ile Pro Ile Pro Asp Pro Tyr Ser Ser Arg Ile Gln Asn Leu Leu
195 200 205

Lys Ile Thr Asn Leu Arg Val Asn Leu Thr Arg Leu His Thr Leu Gly
210 215 220

Asp Asn Leu Leu Asp Pro Arg Arg Glu Ile Arg Glu Lys Tyr Tyr Tyr
225 230 235 240

Ala Leu Tyr Glu Leu Val Ile Arg Gly Asn
245 250

(2) INFORMATION FOR SEQ ID NO:8:

(i) SEQUENCE CHARACTERISTICS:
(A) LENGTH: 40 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:8:

Glu Ala Leu Lys Leu Lys Arg Ala Gly Asn Ser Leu Ala Ala Ser Thr
1 5 10 15

Ala Glu Glu Thr Ala Gly Ser Ala Gln Ser Arg Ala Arg Glu Ala Glu
20 25 30

Lys Gln Leu Arg Glu Gln Val Gly
35 40

(2) INFORMATION FOR SEQ ID NO:9:

(i) SEQUENCE CHARACTERISTICS:
(A) LENGTH: 24 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:9:

Ala Gly Asn Ser Leu Ala Ala Ser Thr Ala Glu Glu Thr Ala Gly Ser
1 5 10 15

Ala Gln Gly Arg Ala Gln Glu Ala
20

(2) INFORMATION FOR SEQ ID NO:10:

(i) SEQUENCE CHARACTERISTICS:
(A) LENGTH: 40 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:10:

```
Glu Glu Leu Arg His Gln Ala Arg Gln Gln Gly Ala Glu Ala Val Gln
1               5                   10                  15

Ala Gln Gln Leu Ala Glu Gly Ala Ser Glu Gln Ala Leu Ser Ala Gln
            20                  25                  30

Glu Gly Phe Glu Arg Ile Lys Gln
        35                  40
```

(2) INFORMATION FOR SEQ ID NO:11:

(i) SEQUENCE CHARACTERISTICS:
(A) LENGTH: 40 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:11:

```
Thr Gly Asp Cys Tyr Ser Gly Asp Glu Asn Pro Asp Ile Glu Cys Ala
1               5                   10                  15

Asp Cys Pro Ile Gly Phe Tyr Asn Asp Pro His Asp Pro Arg Ser Cys
            20                  25                  30

Lys Pro Cys Pro Cys His Asn Gly
        35                  40
```

(2) INFORMATION FOR SEQ ID NO:12:

(i) SEQUENCE CHARACTERISTICS:
(A) LENGTH: 17 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:12:

```
Asp Glu Asn Pro Asp Ile Glu Cys Ala Asp Cys Pro Ile Gly Phe Tyr
1               5                   10                  15

Asn
```

(2) INFORMATION FOR SEQ ID NO:13:

(i) SEQUENCE CHARACTERISTICS:
(A) LENGTH: 40 amino acids
(B) TYPE: amino acid
(D) TOPOLOGY: linear (ii) MOLECULE TYPE: peptide (v) FRAGMENT TYPE: internal (xi) SEQUENCE DESCRIPTION: SEQ ID NO:13:

```
Lys Val Asp Thr Arg Ala Lys Asn Ala Gly Val Thr Ile Gln Asp Thr
1               5                   10                  15

Leu Asn Thr Leu Asp Gly Leu Leu His Leu Met Asp Gln Pro Leu Ser
```

-continued

```
            20                  25                  30

Val Asp Glu Glu Gly Leu Val Leu
        35                  40
```

```
(2) INFORMATION FOR SEQ ID NO:14:

     (i) SEQUENCE CHARACTERISTICS:
          (A) LENGTH: 25 amino acids
          (B) TYPE: amino acid
          (D) TOPOLOGY: linear

    (ii) MOLECULE TYPE: peptide

     (v) FRAGMENT TYPE: internal

    (xi) SEQUENCE DESCRIPTION: SEQ ID NO:14:

Asn Ala Gly Val Thr Ile Gln Asp Thr Leu Asn Thr Leu Asp Gly Leu
1               5                   10                  15

Leu His Leu Met Asp Gln Pro Leu Ser
            20                  25
```

B1K CHAIN OF LAMININ AND METHODS OF USE

"This application is a divisional application of Ser. No. 08/144,121 filed on Oct. 27, 1993, now U.S. Pat. No. 5,610,031. The contents of all of the aforementioned application(s) are hereby incorporated by reference."

This invention was made with government support. The U.S. government may have certain rights in this invention.

BACKGROUND OF THE INVENTION

The present invention relates to adhesion proteins and to methods of using them, e.g., to promote the adhesion of cells to a substrate, e.g., to human dermis. In particular, overlapping cDNA clones encoding the entire laminin B1k chain and recombinant proteins expressed therefrom are disclosed.

The structure of the prototype laminin, a glycoprotein component of most, if not all, basement membranes has been well described in a number of species. Its overall appearance, as visualized by rotary shawdowing, is cross-shaped with a single long arm arising from the coiled-coil interaction of three separate polypeptide chains and three short arms, each originating from the individual polypeptide chains. The three chains are: A, typified by the Ae chain of EHS laminin (400-kD); B1, typified by the B1e chain of EHS laminin (220-kD); and B2, typified by the B2e chain of EHS laminin (210-kD) chains. The primary structure for each of the three prototypic polypeptide chains in humans has been elucidated by overlapping cDNAs.

Additional polypeptides that are related to the laminin chains have been identified. A rat B1 chain homologue, s-laminin (B1s), has been identified. A human A chain homologue, merosin (Am), has been described and is the same as a homologue A chain found in mouse and bovine heart. Both chains can combine with the laminin A, B1 or B2 chains to form the variant trimeric proteins [Ae, B1s, B2e], [Am, B1e, B2e] and [Am, B1s]. A second B1 variant (the sequence of which is a chain based on partial cDNA sequences) from avian eye has been reported and overlapping cDNAs for a human variant B2 chain called laminin B2t have also been described.

Kalinin is an epithelium-specific laminin variant that is the major, if not the only component of the anchoring filament. (The anchoring filament is a characteristic ultrastructural component of the dermal-epidermal junction of skin believed to mediate the adhesion of the epithelium to the basement membrane.) The kalinin molecule contains three disulfide bond-linked polypeptide chains consisting of a 200-kD kalinin A chain (Ak), a 155-kD kalinin B2 chain (B2t), and a 140-kD kalinin B1 chain (B1k). Rotary shadowing of the molecule results in a 107-nm rod with globular domains at each end.

Kalinin is an epithelial-specific cell attachment factor utilized by skin keratinocytes for strengthening their attachment to the underlying dermis. Antibodies to the Ak chain cause the detachment of subconfluent karatino es from their growth substrate and deepithelization of intact skin.

SUMMARY OF THE INVENTION

In general, the invention features a purified DNA including a sequence encoding a B1k chain of laminin.

In preferred embodiments: the DNA encodes the B1k protein of (SEQ ID NO:2); the encoded B1k peptide is at least 80, more preferably 90, and most preferably 95 or 98% homologous with the sequence of (SEQ ID NO:2); the DNA encodes a biologically active B1k.

In another aspect, the invention features a recombinant B1k.

In preferred embodiments: the recombinant B1k protein has the sequence of (SEQ ID NO:2); the recombinant B1k peptide is at least 80, more preferably 90, and most preferably 95 or 98% homologous with the sequence of (SEQ ID NO:2); the recombinant B1k has biological activity.

The invention also includes a vector including a DNA sequence encoding a B1k protein; a cell containing the vector; a method for manufacture of B1k including culturing the cell in a medium to express B1k.

In another aspect, the invention features a purified DNA including (or consisting essentially of) a sequence encoding a fragment of a B1k laminin chain.

In preferred embodiments: the sequence encodes domain VI of B1k, or a kalinin A chain-binding fragment thereof; the sequence encodes a peptide with a biological activity of domain VI of native B1k, e.g., the ability to bind to a kalinin A chain; the sequence encodes any of domain VI, V, IV, III, II, α, or I of B1k.

In other preferred embodiments: the sequence of the encoded B1k fragment is essentially the same as that of a naturally occurring B1k sequence; the DNA sequence which encodes the B1k fragment is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes a B1k fragment hybridizes under high or low stringency to a nucleic acid which encodes a naturally occurring B1k sequence e.g., the amino acid sequence of SEQ ID NO:1; the amino acid sequence of the encoded B1k fragment is less than 30, more preferably less than 40, more preferably less than 50, and most preferably less than 60, 80, 100, or 200 amino acid residues in length; the encoded B1k amino acid sequence is at least 50% more preferably 60%, more preferably 70%, more preferably 80%, more preferably 90%, and most preferably 95% as long as a naturally occurring B1k; the amino acid sequence of the encoded B1k fragment is at least 80%, more preferably at least 85%, yet more preferably at least 90%, yet more preferably at least 95%, and a most preferably at least 98 or 99% homologous with a naturally occurrng B1k sequence, e.g., the sequence of SEQ ID NO:1; the fragment has biological activity.

In other preferred embodiments the fragment includes more than one B1k domain and: the domains in the encoded peptide are arranged in the same relative linear order as found in a naturally B1k; the linear order of the encoded domains is different from that found in a naturally occurring B1k; the domains in the encoded peptide differ in one or more of composition (i.e., which domains are present), linear order, or number (i.e., how many domains are present or how many times a given domain is present) from a naturally occurring B1k.

In another aspect, the invention features, a DNA, preferably a purified DNA, which includes (or consists essentially of) a sequence encoding a fragment of B1k of 20 or more amino acids in length, the peptide having at least 90% homology with an amino acid sequence which is the same, or essentially the same, as a naturally occurring B1k peptide, e.g., the amino acid sequence of SEQ ID NO:2. In preferred embodiments the purified DNA encodes: a peptide which is at least 30, more preferably at least 40, more preferably at least 50, and most preferably at least 60, 80, 100, or 200, amino acid residues in length; the encoded peptide is at least 50% more preferably at least 60%, more preferably 70%, more preferably 80%, more preferably 90%, and most preferably 95% as long as a naturally occurring B1k; a peptide which is at least 80, more preferably at least 85, yet more preferably at least 90, yet more preferably at least 95, and most preferably at least 98 or 99% homologous with an amino acid sequence which is the same, or essentially the same, as a naturally occurring B1k peptide, e.g., the amino acid sequence of SEQ ID NO 2; the peptide has biological activity.

The invention also includes a DNA sequence encoding a B1k fragment; a cell containing the purified DNA; a method for manufacture of a B1k fragment comprising culturing the cell in a medium to express the B1k fragment.

In another aspect, the invention features a peptide which is a fragment of a B1k laminin chain.

In preferred embodiments: the peptide includes (or consists essentially of) domain VI of B1k or a kalinin A chain-binding fragment thereof; the peptide has a biological activity of domain VI of native B1k, e.g., the ability to bind to a kalinin A chain; the peptide includes any of domain VI, V, IV, III, II, α, or I of B1k; the fragment has biological activity.

In other preferred embodiments: the sequence of the peptide is essentially the same as that of a naturally occurring B1k sequence; the DNA sequence which encodes the B1k peptide is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes the B1k peptide hybridizes under high or low stringency to a nucleic acid which encodes a naturally occurring B1k sequence e.g., the amino acid sequence of SEQ ID NO:2; the amino acid sequence of the peptide is less than 30, more preferably less than 40, more preferably less than 50, and most preferably less than 60, 80, 100, or 200 amino acid residues in length; the peptide's amino acid sequence is at least 50% more preferably 60%, more preferably 70%, more preferably 80%, more preferably 90%, and most preferably 95% as long as a naturally occurring B1k; the amino acid sequence of the peptide is at least 80%, more preferably at least 85%, yet more preferably at least 90%, yet more preferably at least 95%, and a most preferably at least 98 or 99% homologous with a naturally occurring B1k sequence, e.g., the sequence of SEQ ID NO:2.

In other preferred embodiments the peptide includes more than one B1k domain and: the domains in the peptide are arranged in the same relative linear order as found in a naturally B1k; the linear order of the domains is different from that found in a naturally occurring B1k; the domains in the peptide differ in one or more of composition (i.e., which domains are present), linear order, or number (i.e., how many domains are present or how many times a given domain is present) from a naturally occurring B1k; the peptide has biological activity.

In another aspect, the invention features a transgenic animal, e.g., a rodent, having a B1k transgene, e.g., a transgene which misexpresses the B1k chain of laminin.

In another aspect, the invention features a method of increasing the permeability of the skin including inhibiting an interaction between B1k and a second molecule, e.g., a kalinin A chain.

In preferred embodiments, the interaction is inhibited by: administering an antibody against a site on kalinin A with which B1k interacts; administering an antibody against a site on B1k, e.g., a site in domain VI, which interacts with the second molecule; administering a fragment of B1k, e.g., a fragment containing domain VI which competes, e.g., competitively or non-competitively with B1k for a site on the second molecule.

In another aspect, the invention features a method of promoting the adhesion of a molecule, e.g., kalinin A or kalinin A- containing molecule, e.g., kalinin or laminin or a cell, e.g., a keratinocyte, to a substrate including providing the substrate coupled, linked, or adhered, to a fragment of B1k which includes domain VI, contacting the molecule or cell, with the B1k domain VI.

In preferred embodiments, the method further includes forming a covalent bond, e.g., a sulfhydral bond, between the molecule or cell and the B1k domain VI.

In another aspect, the invention features a peptide useful for promoting the adhesion of a first molecule or cell, e.g., a keratinocyte, to a second molecule or cell, e.g., a keratinocyte, including a first B1k domain linked to a second B1k domain. (The first domain, e.g., domain VI, binds to the first molecule or cell and the second domain, e.g., domain VI, binds to the second molecule or cell).

In another aspect, the invention features a method of coupling a first molecule or cell to a second molecule or cell including providing a molecule having a first B1k domain and a second B1k domain, linking the first molecule or cell to the first domain, and linking the second molecule or cell to the second domain.

In preferred embodiments: the first and/or second molecule is an adhesion molecule, e.g., laminin, kalinin, or collagen; the first and/or second B1k domain is domain VI or a kalinin A chain-binding fragment thereof of B1k; the first and/or second cell in a keratinocyte.

The invention also includes substantially pure preparation of an antibody, preferably a monoclonal antibody directed against a B1k protein or a fragment of a B1k protein, e.g., a fragment which contains only one domain of B1k; a therapeutic composition including an B1k protein or fragment thereof and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for a disorder, e.g., a disorder of the dermis, e.g., epidermal bulosis, including administering a therapeutically-effective amount of a B1k or fragment thereof to the animal.

In another aspect, the invention features a method for treating an animal, e.g., a human, a mouse, a transgenic animal, or an animal model for a disorder, e.g., a disorder of the dermis, e.g., epidermal bulosis, including administering to the animal cells selected, e.g., selected in vitro, for the expression of a product of the B1k gene, e.g., cells transformed with B1k or B1k fragment-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for a disorder, e.g., a disorder of the dermis, e.g, epidermal bulosis, including administering to the animal a nucleic acid encoding a B1k or fragment thereof and expressing the nucleic acid.

In another aspect, the invention features a method of evaluating the effect of a treatment, e.g., a treatment designed to promote adhesion of a keratinocyte to its substrate including carrying out the treatment and evaluating the effect of the treatment on the expression of the B1k gene.

In preferred emboiments the treatment is administered: to an animal, e.g., a human, a mouse, a transgenic animal, or an animal model for a dermal disorder, e.g., epidermal bulosis, or to a cell, e.g., a cultured cell.

In another aspect, the invention features a method for determining if a subject, e.g., a human, is at risk for a disorder related to mis-expression of the B1k gene, e.g., a disorder of the dermis, e.g., epidermal bulosis, including examining the subject for the expression of the B1k gene, non-wild type expression or mis-expression being indicative of risk.

In another aspect, the invention features a method for determining if a subject, e.g., a human, is at risk for a disorder related to mis-expression of the B1k gene, e.g., a disorder of the dermis, e.g., epidermal bulosis, including providing a nucleic acid sample from the subject and determining if the structure of an B1k gene allele of the subject differs from wild type.

In preferred embodiments: the determination includes determining if an B1k gene allele of the subject has a gross chromosomal rearrangement; the determination includes sequencing the subject's B1k gene.

In another aspect, the invention features, a method of evaluating an animal or cell model for a disorder, e.g., a disorder of the dermis, e.g., epidermal bulosis, including determining if the B1k gene in the animal or cell model is expressed at a predetermined level or if the B1k gene is mis-expressed. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an B1k gene or B1k protein encoding DNA. In preferred embodiments: the B1k gene or DNA includes a deletion, e.g. a deletion of all or part of B1k, e.g., a deletion of all or part of a domain e.g., domain VI, or is otherwise mis-expressed.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the degree of similarity in sequence between two polypeptide molecules or between two nucleic acid molecules. When a position in both of the two compar sequences is occupied by the same base or amino acid monomeric subunit, e.g., if a position in each of two DNA molecules is occupied by adenine, then the molecules are homologous at that position. The homology between two sequences is a finction of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inverted by artifice into a cell and becomes a part of the genome of the animal which develops in whole or part from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at a prenatal, e.g., an embryonic stage.

A substantially pure preparation of a peptide is a preparation which is substantially free of the peptides with which it naturally occurs in a cell. A substantially pure preparation of a non-naturally occurring peptide is one which is at least 10% by weight of the peptide of interest.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild-type in terms of the tissue specificity of expressions, e.g., increased or decreased expression (as compared with wild-type) in a predetermined cell type or tissue type; a pattern of expression that differs from wild type in terms of the length, amino acid sequence, post-translational modification, or a biological activity of a B1k gene product; a patterns of expression that differs from wild-type in terms of the effect of an environmental stimulus or extracellular stimulus on expression of the gene, e.g., a pattern of increased or decreased expression (as compared with wild type) in the presence of an increase or decrease in the strength of the stimulus; or a pattern of isoform expression which differs from wild-type.

A protein or peptide has B1k biological activity if it has one or more of the following properties: the ability to covalently bind via disulfide bond formation with a kalinin B2 chain and a kalinin A chain to form a trimeric protein, kalinin; the ability to bind the kalinin A chain through a covalent disulfide bond formation with domain VI of the B1k chain; the ability to specifically bind type IV collagen; if a B1k domain present on a B1k protein or fragment has a biological property that the domain has when present in the native B1k molecule, e.g., the ability to bind or associate in a specific way with another molecule, e.g., another laminin or kalinin chain or the ability to form a charactstic native rotary shadowy structure characteristic of native B1k.

The molecules of the invention are useful for promoting adhesion of adhesion molecules or keratinocytes to a substrate, e.g., human dermis. The molecules of the invention are also useful for research in cell adhesion. The role of the DNA sequence encoding a peptide having B1k activity and its products can be studied in cells, e.g., cultured cells, transformed with the aforementioned DNA sequence, or fragments thereof, or in transgenic animals. The peptides fragments of the invention allow preparation of antibodies, i.e., monoclonal antibodies, directed against a specific domain.

Other features and advantages of the invention will be apparent from the following description and from the claims.

DETAILED DESCRIPTION

Drawings

The drawings are first briefly described.

FIG. 1 is a map of the B1k region showing (heavy line) start (ATG) and stop codons (TGA), restriction sites (single letter abbreviations), and domains. The light lines below the map show overlapping cDNA clones encoding the entire kalinin B1 chain.

FIG. 2–2C a map of the nucleotide sequence of the laminin B1k chain (SEQ ID NO: 1) and the predicted amino acid sequence (SEQ ID NO: 2) of the B1k peptide chain. Triangles indicate potential O-linked glycosylation sites. Stars indicate potential glycosaminoglycan attachment sites. Potential N-linked glycosylation sites are underlined.

FIGS. 3A–3D are a domain-by-domain comparison of the amino acid sequences of the laminin B1k chain (SEQ ID NO: 3) and the human B1 (SEQ ID NO: 4) chain (B1e).

FIG. 4 is: A) a comparison of the domain sizes and percent identity for the various domains of the laminin B1e and laminin B1k chains; and B) a depiction of the numbering scheme for the laminin B1k domains. The domains are numbered according to their similarity to the comparable domains in the laminin B1e chain. Some of the laminin B1e chain domains are missing in the laminin B1k chain and those that remain are truncated in comparison to the laminin B1e chain.

FIG. 5 is a comparison of the amino acid sequences of domain VI for B1k (SEQ ID NO: 5), B1e (SEQ ID NO: 6), and B1s (SEQ ID NO: 7). The underlined regions are areas where the sequence identity between B1 e and B1s is above average, but the sequence identity with B1 is considerably less than average. The arrow shows an additional cysteine contained by B1k at residue number 50.

FIG. 6 is a compason of peptide sequences of rat lammm B1s (SEQ ID NO: 8), human laminin B1s (SEQ ID NO: 9) and human laminin B1k (SEQ ID NO: 10). Also shown is a comparison of the amino acid sequences of human laminin B2t peptides determined by deduction from cDNA (SEQ ID NO: 11 and SEQ ID NO: 13) (top line) and from sequencing of purified peptide (bottom line) (SEQ ID NO: 12 and SEQ ID NO: 14).

FIG. 7 is a comparison of the cloned cDNA sequence to the B1 and B2 chains of laminin (LAMB1e and LAMB2e), the B2 chain of kalinin (LAMB2t) and the B1 chain of s-laminin (LAMB1s).

cDNA Clones for the Kalinin B1 (Laminin B1k) Chain

The screening of the squamous cell carcinoma cell cDNA expression library with a polyclonal antibody which recognizes human kalinin yielded several positive clones. The fusion proteins from positive clones were adsorbed to nitrocellulose and exposed to the polyclonal antiserum used for the initial screening. Antibodies binding the fusion proteins were individually collected and used for Western blot analysis of partially purified kalinin. Clones were identified that expressed fusion proteins that bound antibodies specific for the 140-kD and the 155/105-kD chain. (The B2 chain is processed from a 155 to a 105 kD form.) Selected clones were sequenced and the predicted amino acid sequences encoded by the cDNAs showed extensive homologies with the B1 and B2 laminin chains. The encoded sequences fro the B1k and B2t chains were confirmed by direct amino acid sequencing of the 140-kD and 155/105-kD kalinin chains.

The nucleotide sequences of the 155/105-kD chain were 99.9% identical to the recently published B2t chain and 100-kD chain of nicein. Protein sequencing of two tryptic peptides from the chain exactly matched derived amino acid sequences, confirming that laminin B2t, the 100-kD nicein chain and the 155/105-kD kalinin chain are identical.

Figure 1:
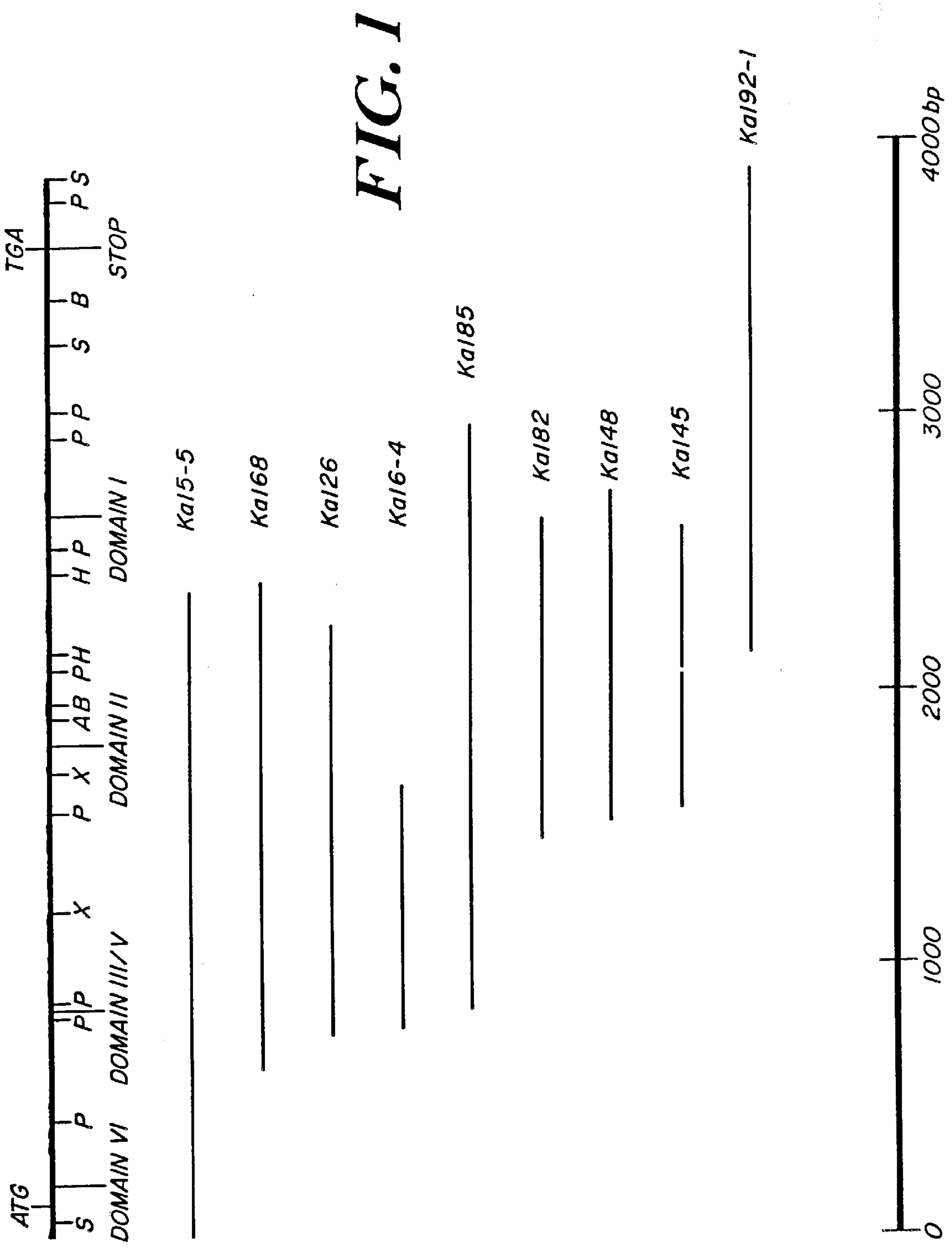
Figure 2:
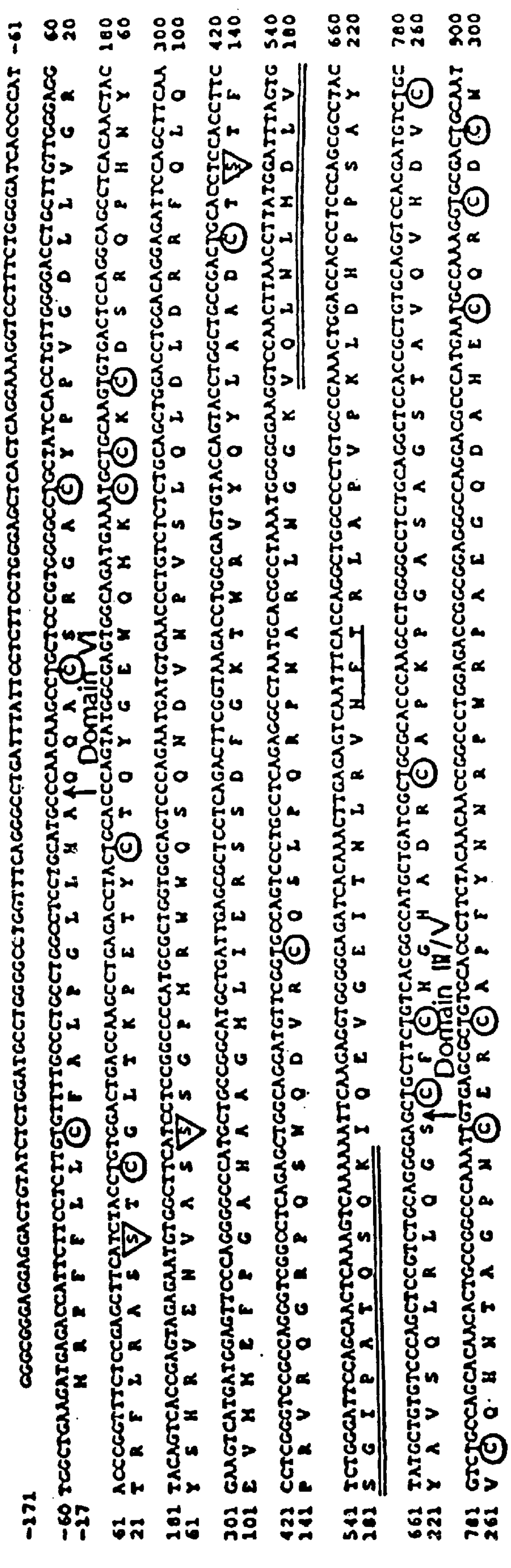
Figure 2A:
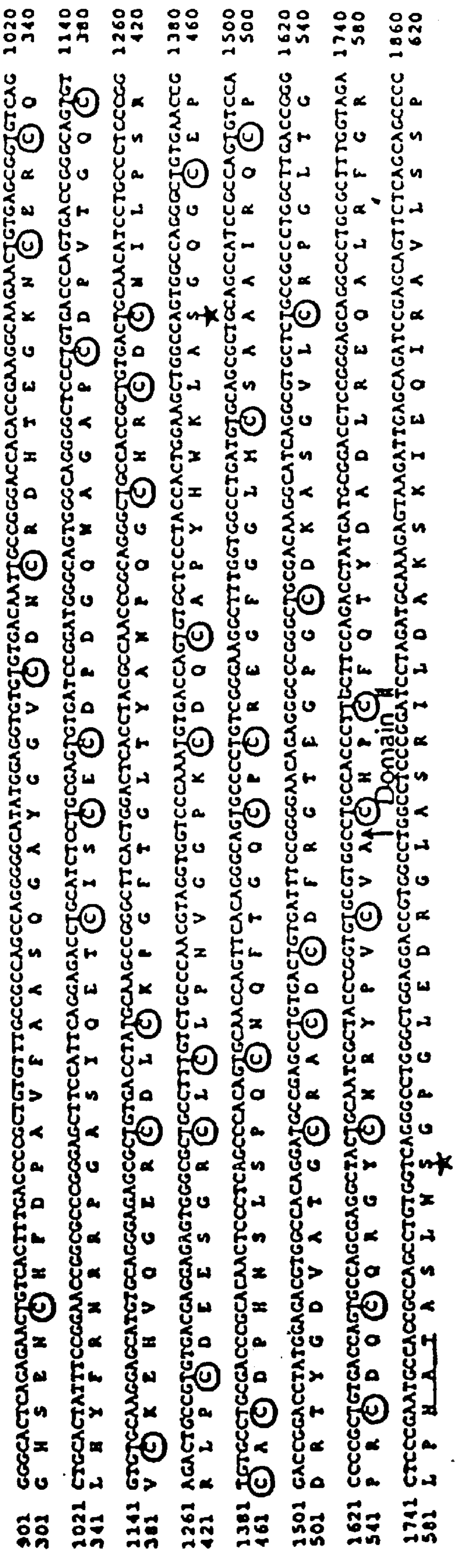
Figure 2B:
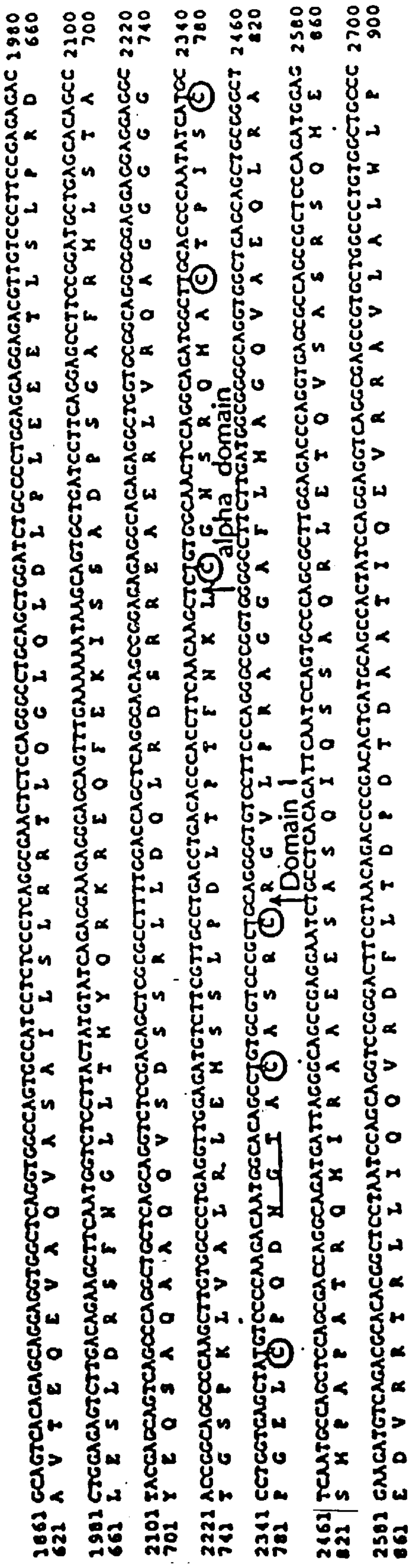
Figure 2C:
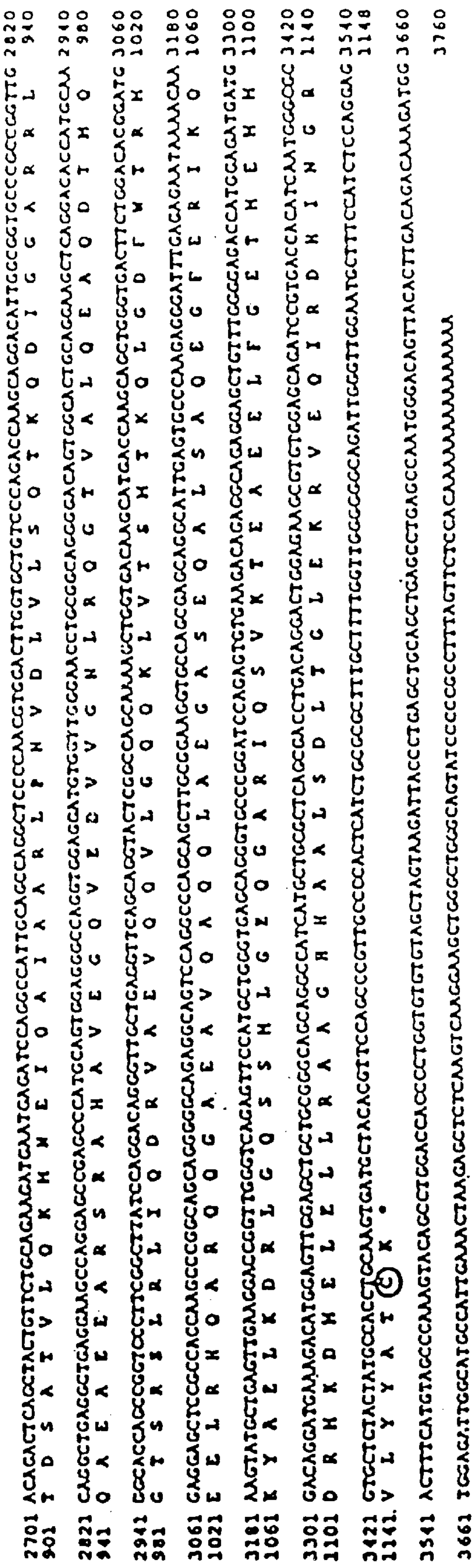

Clones encoding the kalinin 140-kD kalinin B1 chain were selected for further characterization (Kal26, Kal45, Kal48, Kal68, Kal82, and Kal85, FIG. 1). These clones contained 1.5-kb, 0.9-kb, 1.3-kb, 1,8-kb, 1.2-kb, and 2.1-kb inserts, respectively, and nucleotide sequencing demonstrated that the derived amino acid sequences showed extensive similarity to human laminin B1 chain. Rescreening of the cDNA library with Kal45 resulted in the isolation of clones Kal5-5 and Kal6-4 (FIG. 1). These clones contained 2.3-kb and 1.0-kb inserts, respectively. To obtain the 3' end of the cDNA, a 3' RACE procedure (BRL) was used on total mRNA from squamous cell carcinoma media. This resulted in the clone Kal92-1 (1.8-kb). The complete nucleotide sequence of the overlapping clones and the predicted amino acid sequence are shown in FIG. 2.

The immunogen tor polyclonal antiserum against kalinin purified from human keratinocyte-conditioned culture medium has been previously described (Lunstrum et al., 1986; Rousselle et al., 1991).

Isolation of RNA and CDNA synthesis were performed as follows. Ten Costar T-225 flasks were seeded with squamous carcinoma cells (SCC) and allowed to grow until subconfluent. Media was removed and the cells were lysed and total RNA isolated following the guanidium thiocyanate method of Chomczynski and Sacchi, 1987. Poly A+RNA was collected using a Collaborative Research oligo dT Cellulose type 3 column and following company guidelines. Six hundred mg of Poly A+ enriched RNA was sent to Clontech Laboratories (Palo Alto, Calif.) for construction of the Lambda gt11 cDNA library using random primers.

Library screening was performed as follows. The anti-kalinin polyclonal antibody (pAB) was diluted in 1:10 in 10 mM TNT (Tris-HCI, pH 8.0; 150 mM NaCl; 0.05% Tween 20; 3% BSA). *E. coli* (Y-1090 strain) whole cell lysate was added to the diluted antibody and incubated at 4° C. for 24 hours on a nutator. The pre-absorbed antibody was centrifuged at 10,000 rpm for 10 minutes at 4° C. and the supernatant collected. The absorbed antibody was then diluted 1:10 (final dilution 1:100) in TBST (50 mM Tris-HCl, pH 7.9; 150 mM NaCl; 0.05% Tween 20) and 1.2% BSA added. The diluted absorbed antibody was used to screen $8.34\times10^5$ plaques from the unamplified random-primed cDNA library and horseradish peroxidase (HRP) secondary antibody was used to visualize the positive plaques. A total of 89 positive individual plaques were purified in a larger scale and tested again against the antibody.

Epitope determination for phage clones were performed as follows. For each clone, three 150x15 mm LB-ampicillin plates were plated at a density of 6000 pfu and grown 3 hours at 37° C. The plates were overlaid with IPTG saturated nitrocellulose filters and incubated overnight at 37° C. Plates were cooled at 4° C. for 15 minutes and the filters were removed and washed 3 times in TBST (15 min for each wash). The filters were blocked in 4% BSA in TBST for 1 hour at room temperature (RT). Filters were then washed 3 times in TBST. Filters were exposed to the pAB for 3–4 hours at RT followed by 3 washes in TBST. The antibody was eluted from the filter by soaking each filter in 25 ml of 1M acetic acid for 20 minutes. The antibody/acetic acid solution for each of the triplicate samples was pooled and 2 drops of a saturated phenol red solution was added. The solution was neutralized by the addition of an aqueous solution saturated with Tris-HCI and 0.03% BSA was added. The solution was dialyzed against two changes of 1× TBS at 4° C. overnight. The purified antibody solution was collected from the dialysis membrane and a "pinch" of BSA was added. The solution was frozen at −20° C. until needed.

Mini-western blots of purified kalinin were made and exposed to purified antibody from each of the clones for 60-hours at 4° C. Blots were then washed three times in TBST for 15 minutes each. Secondary HRP conjugated antibody was used to illuminate the particular band of kalinin chain corresponding to the clone.

Northern blots were performed as follows. Poly A+RNA was isolated from cell culture of 2 T165 flasks of 70–80% confluent squamous carcinoma cells using Invitrogen's Fast Track RNA isolation systems and exactly following the manufacturer's recommendations. The final RNA pellet was resuspended in 50 ml elution buffer. Twenty mb of Poly A+RNA was used for the gel and subsequent blot using the procedure outlined by Fourney et al. Clone Kal5-5 was radioactively labeled with the Amersham Random labeling system. The blot was placed against X-ray film for 2 hours at −80° C. 3' Rapid Amplification of cDNA Ends (RACE) was performed as follows. A 3' RACE kit was purchased from GIBCO BRL and 1 mg poly A+RNA in 13 ml DEPC-treated water was made into cDNA by reverse transcriptase according to manufacturer's recommendations. The first strand DNA was amplified by PCR following the manufacturer's protocol using the provided antisense poly (T) primer called AP and a specific sense primer for the kalinin B1 chain called D92 (GCT TCA ATG GTC TCC TTA CTA TGT A) (SEQ ID NO:15).

The Laminin B1k Chain Encodes a Distinct Laminin-like Polypeptide

Analysis of the sequence showed that the first possible translated methionine (first amino acid residue, FIG. 2) is followed by a stretch of hydrophobic amino acid residues which are typical for a signal peptide. From the formula for a signal peptide (von Heijne, 1983 and 1986), the signal peptide would be cleaved following Ala17. The 17 residue long signal peptide is followed by an open reading frame of 1148 amino acid residues with a deduced molecular weight of 126,464 daltons. There are 3 putative N-linked glycosylation sites having the predicted residue sequence Asn-X-Ser/Tr, 3 potential O-linked glycosylation sites having the predicted cluster of three or more consecutive Ser and Thr residues and 2 potential glycosaminoglycan attachment consensus sequences, Ser-Gly-X-Gly. In addition there are 120 nucleotides of 5' untranslated sequences and 315 nucleotides of 3' untranslated sequences for a total of 3931 bases. Northern blot analysis showed a single message of 4.0-kb when probed with the cDNA clone Kal5-5.

Protein Sequencing was performed generally as according to Aebersold et al., 1987. Kalinin purified from amnion (Marinkovich et al., 1992a) was run on a polyacrylamide gel in the presence of 2-mercaptoethanol and blotted on a nitrocellulose membrane (Biorad). The 140-kD band was excised and digested by the protease Lys-C. The digested product was separated by HPLC and one fragment was sequenced on an Applied Biosystem sequencer. Computer analysis of the mature polypeptide demonstrated that the laminin B1k chain is most similar to the human laminin B1 chain (LamB1E). A comparison of the laminin B1k polypeptide to this chain is presented in FIG. 3.

Pyroglutamate aminopeptidase reaction was performed generally as according to Andrews et al., 1991. Briefly, kalinin purified from amnion was run on a polyacrylamide gel in presence of 2-mercaptoethanol and blotted on a PVDF membrane in 25 mM Tris, 192 mM glycine, 0.05% SDS and 10% methanol for 4 hours. The 140-kD band was excised, blocked in PVP-40 in 0.1M acetic acid at 37° C. for 30 minutes, washed ten times in water and digested by pyroglutamate aminopeptidase (Boehringer Mannheim) (62.5 mg/mg of protein in 50 mM sodium phosphate, 10 mM EDTA, 5 mM DTT, 5% glycerol, pH 8.0) for 12 hours at 4° C. An additional 62.5 mg of pyroglutamate aminopeptidase/mg of protein was added and digestion was done for 12 hours at 37° C. The blot was washed ten times in water, dried under vacuum and subjected to sequencing on an Applied Biosystem sequencer.

Domain Structure of the Laminin B1k Chain

Since the laminin B1k chain has similarity to the laminin B1e chain, its domains were assigned numbers according to their similarity to the comparable domains in laminin (FIG. 4A). Some of the laminin B1e chain domains are missing in the laminin B1k chain and those that remain are all truncated in comparison to the laminin B1e chain. Specifically, the carboxy-terminal ⅓ of domain V, all of domain IV, and the amino-terminal ⅔ of domain III are missing in the laminin B1k chain. FIG. 4A shows a comparison of the domain sizes and percent identity for the various domains of the laminin B1e and laminin B1k chains. The most amino-terminal domain, domain VI (residues 1–231), is a 231-amino acid residue region containing 9 cystine residues. This domain is likely to form a globular structure similar to domain VI in the laminin B1e chain. Domain III/V (residues 232–559) contains six cysteine-rich EGF modules with three of them similar to comparable modules in domain III (EGF 1, 2, and 3) and three of them similar to comparable modules in domain V (EGF 11, 12, 13) of the laminin B1e chain. The laminin B1k chain has no globular domain IV as is found the in the-laminin B1e chain. Domain II (residues 560–766), as in the laminin B1e chain, begins with two closely spaced cysteins and is predicted to be an α-helical domain containing heptad repeats typical for coiled-coil proteins. Domain I (residues 798–1148) also contains heptad repeats typical for coiled-coil proteins. Just as in laminin B1e, this domain contains a single cysteine residue one residue away from the carobxyl-terminal end. Also similar to the laminin B1e chain is a cysteinerich (6 cysteine residues) a domain that interrupts the helical structures of domains I and II.

Since domain VI is the only globular domain retained by the B1k chain, and since the homologous domain in laminin and s-laminin are believed to mediate self-assembly, the sequences of domain VI for B1k, B1e and B1s were compared (FIG. 5). The amino acid identity of domain VI for B1e and B1s shows 70% sequence conservation (FIG. 5). The number and location of cysteinyl residues is identical. Comparisons of the B1k sequence with these two chains shows 49.8% overall sequence identity. As shown in FIG. 5, B1e and B1s contain several regions within domain VI where the sequence identity is above average. Three of these regions share considerably less than average sequence identity with the B1k chain (FIG. 5, underlined). The B1k chain contains an additional cysteine at amino acid residue number 50 (FIG. 5, arrow). This region is also highly divergent from the B1e and B1s chains with an 18% amino acid residue identity to the B1e chain (excluding the obligatory cysteine) whereas, the same region is 70% identical between B1 e and B1s. These comparisons suggest that B1k shares an overall structural similarity with B1e and B1s, but the chains are likely to be functionally divergent.

The Laminin B1k Chain Is a Truncated Chain

As described above, overlapping cDNA clones encoding the entire 140-kD laminin B1k chain were characterized. The 3.9-kb sequenced corresponds well with the 4.0-kb message size predicted by northern blot analysis. 3' and 5' RACE procedures and were not able to extend the sequence further on either end.

The identity of the cDNAs were confirmed by sequencing a 19-residue long tryptic peptide from the purified 140-kD laminin B1k chain (double-underlined in FIG. 2). Additional protein sequencing of the amino-terminal end of the polypeptide chain confirmed that the end was blocked and therefore most likely began with the residue Gln. After unblocking the end we determined the partial sequence Q-A-C-X-R (X is an indeterminate residue) which corresponds well with our predicted signal peptide cleavage site (start of domain VI, FIG. 2).

The estimated protein size from the cDNAs is 126,464 daltons. This is in contrast to protein data which predicts a protein of about 140,000 daltons. The most likely explanation for this discrepancy is that the chain is glycosylated. There are three potential N-linked glycosylation sites which are underlined in FIG. 2. There are two potential glycosaminoglycan attachment sites marked with stars and three potential O-linked glycosylation sites marked by triangles in FIG. 2. It is interesting to note that the three potential O-linked glycosylation sites are all located in the amino-terminal globular domain, domain VI, which rotary shadowed images predicts to project from the long arm, an ideal position to interact with other molecules such as carbohydrates. In addition, one N-linked glycosylation site is present in the a domain which may extend away from the long arm of the chain and interact with other molecules. The function of the a domain is not known.

The Laminin B1k Chain Is Similar To The Laminin B1e and Laminin B1s Chains

FIG. 7 shows a comparison of our cDNA sequence to the B1 and B2 chains of laminin (LAMB1E and LAMB2E), the B2 chain of kalinin (LAMB2T) and the B1 chain of s-laminin (LAMB1S). Since the kalinin B1 chain is clearly related to these other laminin subunits, the convention of Engel et al., 1991 was followed and the Kalinin B1 chain will be named Laminin B1k. As is apparent from FIG. 7, the human laminin B1k chain is most similar to the human laminin B1e (34.1% identity) and rat laminin B1s (37.1% identity) chains. Initially it seemed possible that the laminin B1k chain might be the human equivalent of the laminin B1s chain since the amino acid residue identity was high when considering comparing two different species. There are two pieces of evidence that show that the laminin B1k chain is distinct from the laminin B1 s chain. The first is the size of the laminin B1k chain polypeptide which was previously reported to be 140-kD. The laminin B1s chain in rat is about 190-kD which is only slightly smaller than the 200-kD laminin B1 e chain. Since there is good conservation of protein size between species (from human to drosophila) for all three of the laminin chains (Laminin Ae, B1e, and B2e), one expects the same will hold true between species for the laminin B1s chain as well and it is predicted that this chain will be 190–200-kD in size. Additional evidence that the laminin B1k chain is distinct from the laminin B1s chain is the fact that a human tryptic peptide sequence was found that is not found in the laminin B1k chain, but has 95.8% identity to the rat laminin B1s chain.

Since the human sequence of the laminin B1s chain is not available, the B1k sequence was compared to the most well described similar molecule, the laminin B1e chain. The major difference between the laminin B1e and laminin B1k chains is their size. The laminin B1k chain has a truncated structure and, therefore, a lower molecular mass than the 200-kD laminin B1e chain. This smaller size is mainly due to the absence of the globular domain which corresponds to domain IV in the laminin B1e chain and to the fact that the corresponding domains III and V are fused into a single domain that is about half the size of the two domain together. There may also be differences in glycosylation between the two polypeptides.

Figure 4:
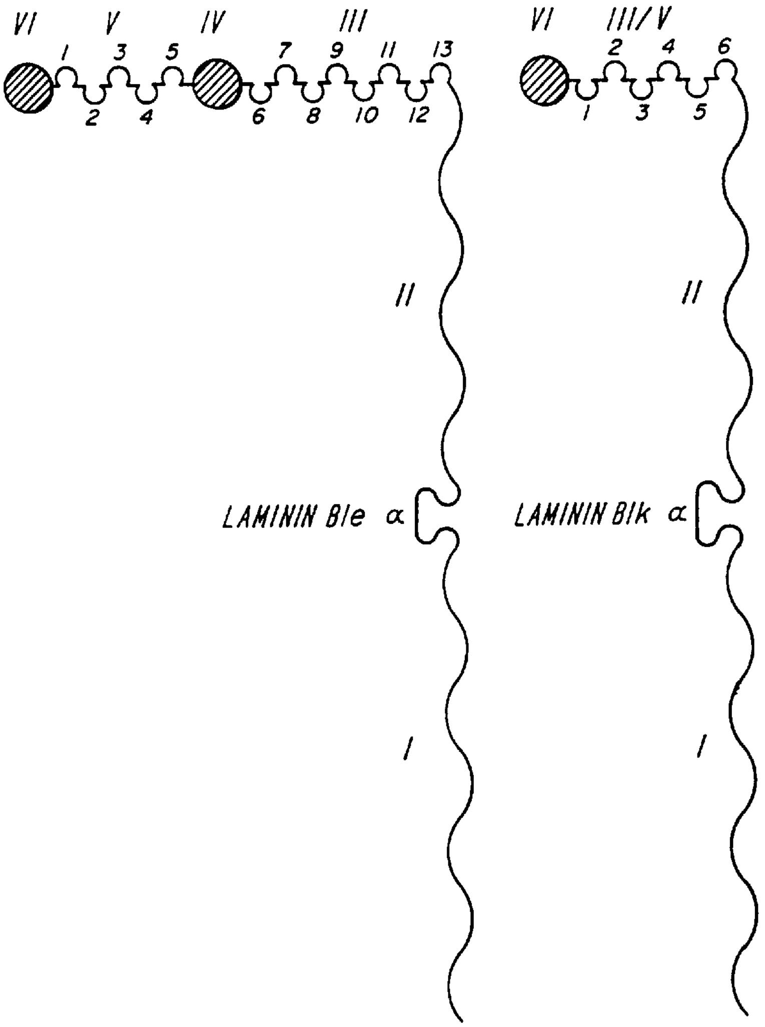

As was found for the laminin B2t chain, the short arms of laminin B1k and laminin B1e have the greatest sequence homology than the long arms (FIG. 4, upper panel: compare domains III–VI, 40–50% identity, to domains I–II, 20–30% identity).

Domain Structure Of The Short Arm Of The Laminin B1k Chain

The greatest functional significance of the short arm is found in the amino-terminal domain VI. In laminin B1e, domain VI has been reported to aid in the self-assembly of the laminin molecules in vitro. The presence of this domain in the laminin B1k chain suggests that this domain could help to organize the extracellular matrix by associating with either other kalinin or laminin molecules. Since this domain is missing in laminin B2t, if the laminin protein associates with other molecules, then this domain is especially crucial in laminin B1k. One possible ligand for this domain is the recently described K-laminin molecule which contains the laminin B1e and B2e chains and a novel A chain. A second candidate for the interaction is type IV collagen which has been reported to bind to the short arms of the laminin B chains.

The comparison of the B1k sequence to B1e and B1s within the VI domain are particularly interesting. The highly divergent amino acid residue identity in certain areas (FIG. 5, underlined) strongly suggests that domain VI of B1k is functionally different from the other known laminin B1 chains. B1k domain VI also contains an odd number of cysteine residues (FIG. 6, arrow), suggesting that one of these is unpaired and available to stabilize interactions of domain VI with another entity. These observations support the hypothesis that kalinin is unlikely to self-assemble through interactions of the VI domains, but rather, the VI domain specifically interacts with the A chain of K-laminin. In tissues, kalinin is disulfide bonded to K-laminin, but not to other laminins that do not contain the K-laminin A chain. Rotary-shadowed images of the adduct suggest that the short arm region of kalinin associates at the crotch of the K-laminin short arms. Since the B1k chain is the only kalinin chain that remains unprocessed in the mature kalinin molecule, the association with K-laminin appears to be mediated by the B1k chain. The significant diversion in sequence homology between the VI domains of B1k versus B1e and B1s, and the presence of a potentially unpaired cysteine residue are consistent with the concept that the B1k VI domain binds the short arm of the K-laminin A chain enabling alignment of an unpaired cysteine in each molecule and subsequent disulfide bond formation.

Domain IV is missing in the laminin B1k chain and while no functions have been reported for the comparable domain in the laminin B1e chain, some investigators reported small peptide sequences in this area can bind to heparin. Since the entire domain is absent in kalinin these sequences are missing.

Two cell-surface binding peptide sequences (PDSGR and YIGSR) have been reported in the EGF repeat number 9 in domain III of the laminin B1e chain. These peptide sequences are not present since the EGF repeats numbered 6–10 are all missing in domain III of the laminin B1k chain.

Domain Structure Of The Long Arm Of The Kalinin B1 Chain

The long arm of the laminin B1k chain contains numerous heptad-repeats similar to those found in the two B chains of larninin. The laminin B1e and B2e chains have been found to associate with one another and are m fact disulfide-bonded. Clearly the three chains of kalinin are disulfide-bonded since they can only be separated by gel electrophoresis only after reduction by β-mercaptoethanol. The 155-kD kalinin chain is known to correspond to the previously reported truncated laminin B2t chain by the cDNAs discussed herein as well as to sequenced tryptic peptides (FIG. 7). The laminin B1k chain appears to interact with the laminin B2t chain by forming an α-helix as is found between the laminin B1e and B2e chains and in fact computer analysis predicts that laminin B1k can form an α-helical coiled-coil structure just as laminin B1e. The laminin B1k and the laminin B2t chain each have a single cysteine in their carboxy-terminal regions that are candidates for disulfide-bonding. The laminin B1k chain also has the short cysteine-rich α domain that divides domains I and II and is predicted to stick out from the long-arm and perform as yet unknown functions.

Finally, adhesion of ciliary ganglion neurons has been attributed to the specific sequence LRE in the laminin B1s chain. This sequence is not found in the laminin B1k chain and this function would therefore be missing.

Other Embodiments

Nucleic acid encoding all or part of the B1k chain can be used to transform cells. For example, the B1k gene, e.g., a mis-expressing or mutant form of the B1k gene, e.g., a deletion, or DNA encoding a B1k chain can be used to transform a cell and to produce a cell in which the cell's genomic B1k gene has been replaced by the transformed gene, producing, e.g., a cell deleted for the B1k gene. Such cells can be used with cells capable of being grown in culture, e.g., cultured stem cells, to investigate the function of the B1k gene.

Analogously, nucleic acid encoding all or part of the B1k gene, e.g., a misexpressing or mutant form of the gene, e.g., a deletion, can be used to transform a cell which subsequently gives rise to a transgenic animal. This approach can be used to create, e.g., a transgenic animal in which the B1k gene is, e.g., inactivated, e.g., by a deletion. Homozygous transgenic animals can be made by crosses between the offspring of a founder transgenic animal. Cell or tissue cultures can be derived from a transgenic animal and the in vivo effects of the laminin B1k chain can subsequently be studied.

The invention includes any fragment of B1k, or any recombinantly produced B1k or fragment thereof which is substantially homologous to a B1k protein, e.g., the B1k protein shown in FIG. 2, or other isoforms. Also included are: allelic variations; natural mutants; induced mutants, e.g., in vitro deletions; proteins encoded by DNA that hybridizes under high (see high stringency conditions defined below) or low (e.g., washing at 2× SSC at 400° C. with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference which provides that high stringency wash for aqueous hybridization is 1 mM $Na_2EDTA$, 40 mM $NaHPO_4$, pH 7.2, and 1% SDS at 65° C.); and polypeptides or proteins specifically bound by antisera to a B1k protein, especially by antisera to the active site or binding domain of a B1k protein. The term also includes chimeric polypeptides that include a B1k protein.

DNA and peptide sequences of the invention can be, e.g., mouse, primate, e.g., human, or non-naturally occurring sequences.

The invention also includes any biologically active fragment or analog of a B1k protein. By "biologically active" is meant possessing any in vivo or in vitro activity which is characteristic of B1k, e.g., B1k activity as described above. Because the B1k protein exhibits a range of physiological properties and because such properties may be attributable to different portions of the B1k protein molecule, a useful B1k protein fragment or B1k protein analog is one which exhibits a biological activity in any one (or more) of a variety of B1k protein assays, for example, the ability to bind the laminin Ak chain, as described above. A B1k protein fragment or analog possesses, most preferably 90%, preferably 40%, or at least 10%, of the activity of a naturally occurring B1k isoform, e.g., of the B1k protein shown in FIG. 2, in any in vivo or in vitro B1k assay.

Preferred analogs include B1k peptides or recombinant B1k proteins or peptides (or biologically active fragments thereof) whose sequences differ from the wild-type sequence by one or more conservative amino acid substitutions or by one or more non-conservative amino acid substitutions, deletions, or insertions which do not abolish biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |

-continued

CONSERVATIVE AMINO ACID REPLACEMENTS

| For Amino Acid | Code | Replace with any of |
|---|---|---|
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-I,eu, Ile, D-Ile, Met, D-Met |

Other useful modifications include those which increase peptide stability; such analogs may contain, for example, one or more non-peptide bonds (which replace peptide bonds) or D-amino acids in the peptide sequence.

Analogs can differ from a naturally occurring B1k protein in amino acid sequence or can modified in ways that do not affect sequence, or both. Analogs of the invention will generaly exhibit at least 70%, more preferably 80%, more preferably 90%, and most preferably 95% or even, 99%, homology with a segment of 20 amino acid residues, preferably more than 40 amino acid residues or more preferably the entire sequence of naturally occurring B1k protein sequence.

Alterations in primary sequence include genetic variations, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

Fragments of B1k proteins or peptides can be made by methods known to those skilled in the art, e.g., by expressing B1k DNA which has been manipulated in vitro to encode the desired fragment; e.g., by restriction digestion or other manipulation of a B1k DNA e.g., the sequence in FIG. 2. Analogs can be made by methods known to those skilled in the art, , e.g., by in vitro DNA sequence modifications of the sequence of a B1k DNA e.g., the sequence in FIG. 2. For example, in vitro mutagenesis can be used to convert the DNA sequence of FIG. 2 into a sequence which encodes an analog in which one or more amino acid residues has undergone a replacement, e.g., a conservative replacement as described in the table of conservative amino acid substitutions provided herein. Fragments or analogs can be tested by methods known to those skilled in the art for the presence of B1k activity.

Also included are B1k protein polypeptides containing residues that are not required for biological activity of the peptide, such as residues that are not required for the biological activity of the polypeptide, or that result from alternative MRNA splicing or alternative protein processing events.

The invention also includes nucleic acids encoding the polypeptides of the invention.

In order to obtain a B1k protein, or fragment thereof, one can insert B1k-encoding DNA into an expression vector, introduce the vector into a cell suitable for expression of the desired protein, and recover and purify the desired protein by prior art methods. Antibodies to B1k proteins can be made by immunizing an animal, e.g., a rabbit or mouse, and recovering anti-B1k antibodies by prior art methods.

Other embodiments are within the following claims.

What is claimed is:

1. A fragment of the B1k chain of laminin of SEQ ID NO:2, said fragment including all or part of domain VI and said fragment being at least about 30 amino acid residues in length, provided that said fragment is not part of a full length B1 k sequence and said fragment has the ability to bind to a K-laminin A chain.

2. The fragment of claim 1, which is at least about 60 amino acid residues in length.

3. The fragment of claim 1, which is at least about 100 amino acid residues in length.

4. The fragment of claim 1, which is at least about 200 amino acid residues in length.

5. A peptide which can be encoded by a nucleic acid which hybridizes under high stringency conditions to SEQ ID NO:1, wherein said peptide includes all or part of dome VI and said peptide is at least 30 amino acid residues in length, provided that said peptide is not part of a full length B1k sequence and said peptide has the ability to bind to a K-laminin A chain.

6. The peptide of claim 5, which is at least about 60 amino acid residues in length.

7. The peptide of claim 5, which is at least about 100 amino acid residues in length.

8. The peptide of claim 5, which is at least about 200 amino acid residues in length.

9. A therapeutic composition comprising the fragment of claim 1 or the peptide of claim 5 and a pharmaceutically acceptable carrier.

* * * * *